(12) United States Patent
Dyker et al.

(10) Patent No.: US 6,355,615 B1
(45) Date of Patent: Mar. 12, 2002

(54) DESOXYCYCLODEPSIPEPTIDES AND THEIR USE FOR COMBATTING ENDOPARASITES

(75) Inventors: Hubert Dyker, Köln (DE); Jürgen Scherkenbeck, Clearwater Bay (HK); Achim Harder, Köln (DE); Norbert Mencke, Leverkusen (DE); Georg von Samson-Himmelstjerna, Solingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/424,803

(22) PCT Filed: May 25, 1998

(86) PCT No.: PCT/EP98/03059

§ 371 Date: Nov. 29, 1999

§ 102(e) Date: Nov. 29, 1999

(87) PCT Pub. No.: WO98/55469

PCT Pub. Date: Dec. 10, 1998

(30) Foreign Application Priority Data

Jun. 4, 1997 (DE) .......................................... 197 23 320
Mar. 9, 1998 (DE) .......................................... 198 10 017

(51) Int. Cl.[7] .................... C07D 273/00; C07D 413/10; C07D 413/14; A61K 31/395
(52) U.S. Cl. .......................... 514/11; 530/323; 530/345
(58) Field of Search ................................. 514/9, 11, 16, 514/18; 530/317, 323, 328, 330, 345

(56) References Cited

FOREIGN PATENT DOCUMENTS

| EP | 382173 | * | 8/1990 |
| EP | 626376 | * | 11/1994 |
| EP | 634408 | * | 1/1995 |
| EP | 718293 | * | 6/1996 |

OTHER PUBLICATIONS

Kopka, Selective Semisynthetic Modification of L–156, 602 . . . Tet. Lett. vol. 31, No. 33, pp. 4711–4714, 1990.*
J. Org. Chem, vol. 38, Jan.–Apr., 1973, pp. 912–916, Brown et al, "Selective Reductions XVIII. The Fast Reaction of Primary, Secondary, and Tertiary Amides with Diborane. A Simple Convenient Procedure for the Conversion of Amides to the Corresponding Amines".
J. Antibiotics, vol. 45, May 1992, pp. 692–697, Sasaki, et al, "A New Anthelmintic Cyclodepsipeptide, PF 1022A".

* cited by examiner

*Primary Examiner*—Jeffrey E. Russel
(74) *Attorney, Agent, or Firm*—Joseph C. Gil; Godfried R. Akorli

(57) ABSTRACT

The invention relates to novel deoxycyclodepsipeptides which are prepared from cyclodepsipeptides having 24 ring members which are constructed from alternating α-aminocarboxylic acids and α-hydroxycarboxylic acids, by complete or partial chemoselective reduction of the carbonyl groups of the amide function to give methylene groups using suitable reduction processes, and to mixtures and derivatives thereof. The deoxycyclodepsipeptides according to the invention have anthelmintic activity.

11 Claims, No Drawings

DESOXYCYCLODEPSIPEPTIDES AND THEIR USE FOR COMBATTING ENDOPARASITES

The invention relates to novel deoxycyclodepsipeptides, to processes for their preparation and to their use for controlling parasites, in particular helminths, in veterinary and human medicine.

Various cyclodepsipeptides having antiparasitic activity are described in the literature. EP-A 382 173 discloses a cyclooctadepsipeptide designated PF 1022. EP-A 626 376, EP-A 634 408 and EP-A 718 293 disclose further 24-membered cyclodepsipeptides. Their anthelmintic activity is not in all cases satisfactory.

The invention relates to novel deoxycyclodepsipeptides which are prepared from cyclodepsipeptides having 24 ring members which are constructed from alternating α-aminocarboxylic acids and α-hydroxycarboxylic acids, by complete or partial chemoselective reduction of the carbonyl groups of the amide function to give methylene groups using suitable reduction processes, and to mixtures and derivatives thereof.

The cyclodepsipeptides employed as starting materials are constructed from alternating 4 α-aminocarboxylic acids and 4 α-hydroxycarboxylic acid-units.

α-Aminocarboxylic acids are natural or synthetic amino acids which may be identical or different. They may be N-alkylated, i.e. substituted by a straight-chain or branched $C_{1-4}$-alkyl group, preferably a methyl group, which for its part may also be substituted.

α-Hydroxycarboxylic acids are natural and synthetic 2-hydroxycarboxylic acids which may be identical or different.

Complete or partial chemoselective reduction means that one or more amidic carbonyl groups (C=O adjacent to N) are reduced without the ester carbonyl groups (C=O adjacent to O) in the cyclodepsipeptide skeleton being attacked.

The reduction is carried out either directly or in a multi-stage process, depending on the reducing agent chosen.

Complete or partial reduction means that, for example, in an octadepsipeptide having 4 amidic carbonyl groups, all 4 of the carbonyl groups in question or 1 to 3 of these carbonyl groups are reduced.

The reduction generally yields mixtures of the deoxydepsipeptides in varying degrees of reduction. The individual components are present in varying proportions, depending on the stoichiometry and the kind of reduction process. Homogeneous deoxydepsipeptides are obtained from the mixtures by employing the customary physical or chemical separation processes.

The products obtained in the reduction can be converted chemically into further derivatives.

The deoxycyclodepsipeptides according to the invention can be characterized by the formula (I):

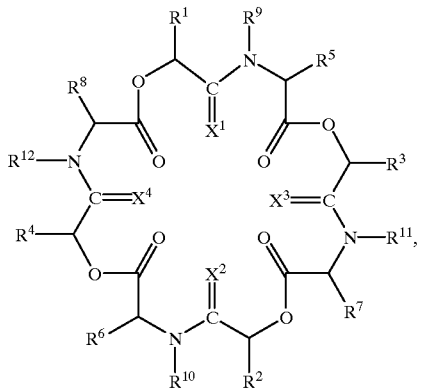

(I)

in which
$C=X^1$, $C=X^2$, $C=X^3$ and $C=X^4$ independently of one another each represent one of the groups CO, CS or $CH_2$, where at least one of these groups represents $CH_2$, $R^1$ and $R^2$ independently of one another each represent hydrogen, alkyl, hydroxymethyl or alkoxymethyl, $R^3$ and $R^4$ independently of one another each represent alkyl or represent phenyl or benzyl, each of which is optionally mono- or polysubstituted by radicals W, where
W represents halogen, nitro, cyano, carbonyl, alkoxycarbonyl, alkyl, —CH($R^{13}$)$NR^{14}R^{15}$, alkenyl, alkoxycarbonylalkenyl, alkynyl, alkoxycarbonylalkynyl, hydroxyl, alkoxy, alkoxyalkoxy, alkoxyalkoxyalkoxy, dialkylaminoalkoxy, respectively optionally substituted aryl, arylalkyl, aryloxy or arylmethoxy, represents heterocyclylmethoxy, —$NR^{16}R^{17}$, —$SO_2$—NR $R^{16}R^{17}$, —$SR^{18}$, —S(O) $R^{18}$ or —$S(O)_2R^{18}$, $R^{13}$ represents hydrogen or carboxyl, $R^{14}$ represents hydrogen, alkyl, optionally halogen-substituted alkylcarbonyl or benzoyl or $R^{13}$ and $R^{14}$ together represent a radical —$(CH_2)_n$—CO—, where n=2, 3 or 4, $R^{15}$ represents hydrogen, alkyl, optionally halogen-substituted alkylcarbonyl or benzoyl or $R^{14}$ and $R^{15}$ together represent a radical —$(CH_2)_o$—CO—, where o=3, 4 or 5, represent a diacyl radical of a $C_4$–$C_6$-dicarboxylic acid or represent optionally halogen-substituted phthaloyl, $R^{16}$ represents hydrogen, optionally halogen-, hydroxyl- or alkoxy-substituted alkyl, represents heterocyclylmethyl, formyl, alkylcarbonyl or optionally substituted arylmethyl or benzoyl or represents the radical —CO—$CR^{19}R^{20}$—$NR^{21}R^{22}$ and $R^{17}$ represents hydrogen, optionally halogen-, hydroxyl- or alkoxy-substituted alkyl, represents heterocyclylmethyl, alkylcarbonyl or optionally substituted arylmethyl or benzoyl, $R^{16}$ and $R^{17}$ together represent optionally substituted phthaloyl or, together with the linking nitrogen atom, represent an optionally substituted mono- or polycyclic, optionally bridged and/or spirocyclic, saturated or unsaturated heterocycle which may contain one to 3 further hetero atoms from the group consisting of nitrogen, oxygen and sulfur, $R^{18}$ represents alkyl or optionally substituted phenyl or benzyl, $R^{19}$ represents one of the radicals of a natural or synthetic α-amino acid, where functional groups may optionally be protected, $R^{20}$ represents hydrogen, alkyl or phenyl, $R^{19}$ and $R^{20}$ together represent —$(CH_2)_p$—, where p=2, 3, 4 or 5, or represent —$(CH_2)_2$—$NR^{23}$—$(CH_2)_2$—, where $R^{23}$ represents alkyl, phenyl or benzyl, $R^{21}$ represents hydrogen or alkyl, $R^{19}$ and $R^{21}$ together represent —$(CH_2)_3$— and —$(CH_2)_4$— and $R^{22}$ represents hydrogen or a protective group known from peptide chemistry, such as acetyl, tert-butoxy carbonyl (Boc), benzyl-oxycarbonyl (Cbz) or benzyl (Bzl), $R^5$, $R^6$, $R^7$ and $R^8$ independently of one another each represent hydrogen, optionally amino- or hydroxyl-substituted alkyl, represent mercaptomethyl, methylthioethyl, carboxymethyl, carboxyethyl, carbamoylmethyl, carbamoylethyl, guanidinopropyl, represent optionally amino-, nitro-, halogen-, hydroxyl- or methoxy-substituted phenyl or benzyl, represent naphthylmethyl, indolylmethyl, imidazolylmethyl, triazolylmethyl or pyridylmethyl, where functional groups may optionally be protected, and $R^9$, $R^{10}$, $R^{11}$ and $R^{12}$ independently of one another each represent hydrogen or optionally substituted $C_1$–$C_4$-alkyl.

The protective groups known from peptide chemistry are listed, for example, in T. W. Greene, P. G. M. Wuts, Protective Groups in Organic Synthesis, $2^{nd}$ Ed., John Wiley & Sons, New York 1991.

The configuration at the chiral carbons is immaterial, i.e. the compounds of the formula (I) according to the invention are constructed from D- and/or L-configured amino acids and hydroxycarboxylic acids. The invention provides the pure stereoisomers and mixtures thereof. The compounds are preferably constructed from alternating D-hydroxycarboxylic acids and L-amino acids.

The invention furthermore provides a process for preparing the compounds according to the invention, characterized in that cyclodepsipeptides which have been prepared by fermentation or synthetically and which have 24 ring members a) are reduced with borane (boron hydride) or complex hydrides in the presence of metal salts, or b) are reacted with a sulfurizing agent and subsequently reduced with complex hydrides in the presence of metal salts and the compounds according to the invention obtained by one of the processes a) or b) are optionally derivatized further.

Furthermore, it has been found that the compounds according to the invention are outstandingly suitable for controlling helminths in human and veterinary medicine.

The formula (I) given above defines preferred compounds according to the invention.

$C=X^1$, $C=X^2$, $C=X^3$ and $C=X^4$ independently of one another each preferably represent one of the groups CO, CS or $CH_2$, where at least one of these groups represents $CH_2$.

$R^1$ and $R^2$ independently of one another each preferably represent hydrogen, $C_1$–$C_6$-alkyl, hydroxymethyl or $C_1$–$C_6$-alkoxymethyl.

$R^3$ and $R^4$ independently of one another each preferably represent $C_1$–$C_6$-alkyl or phenyl or benzyl, each of which is optionally mono- or disubstituted by a radical W.

$R^5$, $R^6$, $R^7$ and $R^8$ independently of one another each preferably represent hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 4-methoxybenzyl, 2-nitrobenzyl, 3-nitrobenzyl, 4-nitrobenzyl, 2-aminobenzyl, 3-aminobenzyl, 4-aminobenzyl, 3,4-dichlorobenzyl, 4-iodobenzyl, (α-naphthylmethyl, β-naphthylmethyl, 3-indolylmethyl, 4-imidazolylmethyl, 1,2,3-triazol-1-yl-methyl, 1,2,4-triazol-1-yl-methyl, 2-pyridylmethyl or 4-pyridylmethyl, where functional groups may optionally be protected.

$R^9$, $R^{10}$, $R^{11}$ and $R^{12}$ independently of one another each preferably represent hydrogen, methyl or ethyl.

W preferably represents halogen, nitro, cyano, carbonyl, $C_1$–$C_6$-alkoxycarbonyl, $C_1$–$C_6$-alkyl, —$CH(R^{13})$ $NR^{14}R^{15}$, $C_2C_6$-alkenyl, $C_1$–$C_6$-alkoxycarbonyl-$C_2$–$C_4$-alkenyl, $C_2$–$C_6$-alkynyl, $C_1$–$C_6$-alkoxycarbonyl-$C_2$–$C_4$-alkynyl, hydroxyl, $C_1$–$C_6$-alkoxy, $C_1$–$C_6$-alkoxy-$C_1$–$C_6$-alkoxy, $C_1$–$C_6$-alkoxy-$C_1$–$C_6$-alkoxy-$C_1$–$C_6$-alkoxy, di-($C_1$–$C_6$-alkyl)-amino-$C_2$–$C_6$-alkoxy, represents phenyl, benzyl, phenoxy or benzylmethoxy, each of which is optionally mono- to trisubstituted independently of one another by halogen, nitro, cyano, $C_1$–$C_4$-alkyl, $C_1$–$C_4$-alkoxy, $C_1$–$C_4$-halogenoalkoxy, hydroxyl or amino, represents heterocyclylmethoxy having a 5- to 6-membered monocycle or 8- to 10-membered bicycle having 1 to four hetero atoms selected from 1 to 4 nitrogen atoms, 1 to 2 oxygen and/or 1 to 2 sulfur atoms, represents —$NR^{16}R^{17}$, —$SO_2$—$NR^{16}R^{17}$, —$SR^{18}$, —$S(O)R^{18}$ or —$S(O)_2R^{18}$.

$R^{13}$ preferably represents hydrogen or carboxyl.

$R^{14}$ preferably represents hydrogen, $C_1$–$C_6$-alkyl, optionally fluorine- or chlorine-substituted $C_1$–$C_6$-alkylcarbonyl or benzoyl.

$R^{13}$ and $R^{14}$ together also preferably represent a radical —$(CH_2)_n$—CO—, where n=2, 3 or 4.

$R^{15}$ preferably represents hydrogen, $C_1$–$C_6$-alkyl, $C_1$–$C_6$-alkylcarbonyl or benzoyl.

$R^{14}$ and $R^{15}$ together also preferably represent a radical —$(CH_2)_o$—CO—, where o=3, 4 or 5, represent a diacyl radical of a $C_4$–$C_6$-dicarboxylic acid or represent optionally halogen-substituted phthaloyl.

$R^{16}$ preferably represents hydrogen, optionally halogen-, hydroxyl- or $C_1$–$C_6$-alkoxy-substituted $C_1$–$C_6$-alkyl, represents heterocyclylmethyl having a 5- to 6-membered monocycle or 8- to 10-membered bicycle having 1 to four hetero atoms selected from 1 to 4 nitrogen atoms, 1 to 2 oxygen and/or 1 to 2 sulfur atoms, represents formyl, $C_1$–$C_6$-alkylcarbonyl or represents benzyl or benzoyl, each of which is optionally mono- to trisubstituted independently of one another by halogen, nitro, cyano, $C_1$–$C_4$-alkyl or $C_1$–$C_4$-alkoxy, or represents the radical —CO—$R^{19}R^{20}$—$NR^{21}R^{22}$.

$R^{17}$ preferably represents hydrogen, optionally halogen-, hydroxyl- or $C_1$–$C_6$-alkoxy-substituted $C_1$–$C_6$-alkyl, represents heterocyclylmethyl having a 5- to 6-membered monocycle or 8- to 10-membered bicycle having 1 to four hetero atoms selected from 1 to 4 nitrogen atoms, 1 to 2 oxygen and/or 1 to 2 sulfur atoms, represents $C_1$–$C_6$-alkylcarbonyl or represents benzyl or benzoyl, each of which is optionally mono- to trisubstituted independently of one another by halogen, nitro, cyano, $C_1$–$C_4$-alkyl or $C_1$–$C_4$-alkoxy.

$R^{16}$ and $R^{17}$ together also preferably represent halogen-, nitro-, cyano-, $C_1$–$C_4$-alkyl- or $C_1$–$C_4$-alkoxy-substituted phthaloyl or, together with the linking nitrogen atom, represent an optionally halogen-, $C_1$–$C_4$-alkyl- or $C_1$–$C_4$-alkoxy-substituted and optionally N-acylated monocyclic heterocycle having 3 to 8 ring members or bicyclic heterocycle having 7 to 11 ring members which is optionally bridged and/or spirocyclic, optionally condensed with one or two carbocyclic ring systems, saturated or unsaturated and may contain 1 to 3 further hetero atoms from the group consisting of 1 to 3 nitrogen atoms, 1 oxygen atom and 1 sulfur atom.

$R^{18}$ preferably represents methyl, ethyl or represents phenyl or benzyl, each of which is optionally mono- or disubstituted independently of one another by fluorine, chlorine, nitro, methyl, trifluoromethyl or methoxy.

$R^{19}$ preferably represents hydrogen, optionally amino- or hydroxyl-substituted $C_1$–$C_4$-alkyl or represents mercaptomethyl, methylthioethyl, carboxymethyl, carboxyethyl, carbamoylmethyl, carbamoylethyl, guanidinopropyl or represents optionally amino-, nitro-, halogen-, hydroxyl- or methoxy-substituted phenyl or benzyl or represents naphthylmethyl, indolylmethyl, imidazolylmethyl, triazolylmethyl or pyridylmethyl, where functional groups may optionally be protected.

$R^{20}$ preferably represents hydrogen, $C_1$–$C_4$-alkyl or phenyl.

$R^{19}$ and $R^{20}$ together also preferably represent —$(CH_2)_p$—, where p=2, 3, 4 or 5, or represent —$(CH_2)_2$—$NR^{23}$—$(CH_2)_2$—, where $R^{23}$ represents $C_1$–$C_4$-alkyl, phenyl or benzyl.

$R^{21}$ preferably represents hydrogen or $C_1$–$C_4$-alkyl.

$R^{19}$ and $R^{21}$ together also preferably represent —$(CH_2)_3$— and —$(CH_2)_4$—.

$R^{22}$ preferably represents hydrogen or a protective group known from peptide chemistry, such as acetyl, tert-butoxycarbonyl, benzyloxycarbonyl or benzyl.

$C=X^1$, $C=X^2$, $C=X^3$ and $C=X^4$ independently of one another each particularly preferably represent one of the groups CO, CS or $CH_2$, where at least one of these groups represents $CH_2$.

$R^1$ and $R^2$ independently of one another each particularly preferably represent hydrogen, $C_1$–$C_4$-alkyl, hydroxymethyl or $C_1$–$C_4$-alkoxymethyl.

$R^3$ and $R^4$ independently of one another each particularly preferably represent phenyl or benzyl, each of which is optionally substituted by a radical W.

$R^5$, $R^6$, $R^7$ and $R^8$ independently of one another each particularly preferably represent methyl, iso-propyl, iso-butyl, sec-butyl, hydroxymethyl, benzyl, 4-hydroxy-benzyl, where hydroxyl groups may optionally be protected.

$R^9$, $R^{10}$, $R^{11}$ and $R^{12}$ independently of one another each particularly preferably represent hydrogen, methyl.

W particularly preferably represents fluorine, chlorine, bromine, iodine, nitro, cyano, carbonyl, $C_1$–$C_4$-alkoxycarbonyl, $C_1$–$C_4$-alkyl, —$CH(R^{13})NR^{14}R^{15}$, $C_2$–$C_6$-alkenyl, $C_1$–$C_4$-alkoxycarbonyl-$C_2$–$C_4$-alkenyl, $C_2$–$C_4$-alkenyl, $C_1$–$C_4$-alkoxycarbonyl-$C_2$–$C_4$-alkynyl, hydroxyl, $C_1$–$C_4$-alkoxy, $C_1$–$C_4$-alkoxy-$C_1$–$C_4$-alkoxy, $C_1$–$C_4$-alkoxy-$C_1$–$C_4$-alkoxy-$C_1$–$C_4$-alkoxy, di-($C_1$–$C_4$-alkyl)-amino-$C_2$–$C_4$-alkoxy, represents phenyl, benzyl, phenoxy or benzylmethoxy, each of which is optionally mono- or disubstituted independently of one another by fluorine, bromine, nitro, cyano, $C_1$–$C_4$-alkyl, fluorine- and/or chlorine-substituted methyl or ethyl, $C_1$–$C_4$-alkoxy, trifluoromethoxy, hydroxyl or amino, represents furylmethoxy, benzofurylmethoxy, thienylmethoxy, pyrrolylmethoxy, indolylmethoxy, imidazolylmethoxy, pyridylmethoxy, —$NR^{16}R^{17}$ or —$SO_2$—$NR^{16}R^{17}$.

$R^{13}$ particularly preferably represents hydrogen or carboxyl.

$R^{14}$ particularly preferably represents hydrogen, $C_1$–$C_4$-alkyl, benzoyl or $C_1$–$C_4$-alkylcarbonyl which is optionally mono- to trisubstituted by fluorine or chlorine.

$R^{13}$ and $R^{14}$ together also particularly preferably represent a radical —$(CH_2)_n$—CO—, where n=2, 3 or 4.

$R^{15}$ particularly preferably represents hydrogen or methyl, ethyl, n-propyl, isopropyl, n-butyl, isobutyl, tert-butyl.

$R^{14}$ and $R^{15}$ together also particularly preferably represent a radical —$(CH_2)_o$—CO—, where o=3, 4 or 5, represent a diacyl radical of a $C_4$–$C_6$-dicarboxylic acid or represent phthaloyl which is optionally mono- or polysubstituted by chlorine or fluorine.

$R^{16}$ particularly preferably represents hydrogen, methyl, ethyl, n-propyl, isopropyl, n-butyl, isobutyl, sec-butyl or tert-butyl, represents methyl, ethyl or n-propyl, each of which is monosubstituted by chlorine, bromine, hydroxyl, methoxy or ethoxy, represents furylmethyl, benzofurylmethyl, thienylmethyl, pyrrolylmethyl, indolylmethyl, imidazolylmethyl, pyridylmethyl, represents formyl, $C_1$–$C_4$-alkylcarbonyl or represents benzyl or benzoyl, each of which is optionally mono- or disubstituted independently of one another by fluorine, chlorine, bromine, iodine, nitro, cyano, $C_1$–$C_4$-alkyl, or $C_1$–$C_4$-alkoxy, or represents the radical —CO—$CR^{19}R^{20}$—$R^{21}R^{22}$.

$R^{17}$ particularly preferably represents hydrogen or, depending on $R^{16}$, an identical radical from the group: methyl, ethyl, n-propyl, isopropyl, n-butyl, isobutyl, sec-butyl or tert-butyl, methyl, ethyl or n-propyl which are monosubstituted by chlorine, bromine, hydroxyl, methoxy or ethoxy, represents furylmethyl, benzofurylmethyl, thienylmethyl, pyrrolylmethyl, indolylmethyl, imidazolylmethyl, pyridylmethyl or benzyl which is optionally mono- or disubstituted independently of one another by fluorine, chlorine, bromine, iodine, nitro, cyano, $C_1$–$C_4$-alkyl or $C_1$–$C_4$-alkoxy.

$R^{16}$ and $R^{17}$ together also particularly preferably represent phthaloyl which is optionally mono- to tetrasubstituted by fluorine, chlorine or methyl and/or mono- or disubstituted by bromine, nitro, cyano, $C_2$–$C_4$-alkyl or methoxy, or, together with the linking nitrogen atom, represent an optionally fluorine-, chlorine-, methyl-, ethyl-, n-propyl-, isopropyl-, methoxy- or ethoxy-substituted and optionally $C_1$–$C_4$-alkylcarbonyl-N-acylated monocyclic heterocycle having 3 to 8 ring members or bicyclic heterocycle having 7 to 11 members which is optionally bridged and/or spirocyclic, optionally condensed with one or two carbocyclic ring systems, saturated or unsaturated and may contain 1 to 3 further hetero atoms from the group consisting of 1 to 3 nitrogen atoms, 1 oxygen atom and 1 sulfur atom.

$R^{19}$ particularly preferably represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 4-methoxybenzyl, 2-nitrobenzyl, 3-nitrobenzyl, 4-nitrobenzyl, 2-aminobenzyl, 3-aminobenzyl, 4-aminobenzyl, 3,4-dichlorobenzyl, 4-iodobenzyl, (α-naphthylmethyl, β-naphthylmethyl, 3-indolylmethyl, 4-imidazolylmethyl, 1,2,3-triazol-1-yl-methyl, 1,2,4-triazol-1-yl-methyl, 2-pyridylmethyl or 4-pyridylmethyl, where functional groups may optionally be protected.

$R^{20}$ particularly preferably represents hydrogen, $C_1$–$C_4$-alkyl or phenyl.

$R^{19}$ and $R^{20}$ together also particularly preferably represent —$(CH_2)_p$—, where p=2, 3, 4 or 5, or represent —$(CH_2)_2$—$NR^{23}$—$(CH_2)_2$—, where $R^{23}$ represents $C_1$–$C_4$-alkyl, phenyl or benzyl.

$R^{21}$ particularly preferably represents hydrogen or $C_1$–$C_4$-alkyl.

$R^{19}$ and $R^{21}$ together also particularly preferably represent —(CH$_2$)$_3$— and —(CH$_2$)$_4$—.

$R^{22}$ particularly preferably represents hydrogen or a protective group known from peptide chemistry, such as acetyl, tert-butoxycarbonyl, benzyloxycarbonyl or benzyl.

C=X$^1$, C=X$^2$, C=X$^3$ and C=X$^4$ independently of one another each very particularly preferably represent one of the groups CO or CH$_2$, where at least one of these groups represents CH$_2$.

$R^1$ and $R^2$ independently of one another each very particularly preferably represent methyl, hydroxymethyl or methoxymethyl.

$R^3$ and $R^4$ independently of one another each very particularly preferably represent benzyl which is optionally substituted by a radical W.

$R^5$, $R^6$, $R^7$ and $R^8$ independently of one another each very particularly preferably represent iso-propyl, iso-butyl or sec-butyl.

$R^9$, $R^{10}$, $R^{11}$ and $R^{12}$ each very particularly preferably represent methyl.

W very particularly preferably represents bromine, iodine, nitro, cyano, carbonyl, methoxycarbonyl, ethoxycarbonyl, —CH(R$^{13}$)NR$^{14}$R$^{15}$, 2-oxo-pyrrolidin-5-yl, 2-oxo-piperidin-6-yl, 2-methoxycarbonyl-vinyl, 2-methoxycarbonyl-ethynyl, hydroxyl, methoxy, 2-methoxy-ethoxy, 2-dimethylamino-ethoxy, represents phenyl, benzyl, phenoxy or benzylmethoxy, each of which is optionally mono- or disubstituted independently of one another by fluorine, bromine, nitro, cyano, methyl, ethyl, trifluoromethyl, difluoromethyl, chlorodifluoromethyl, trichloromethyl, methoxy, ethoxy, trifluoromethoxy, hydroxyl or amino, represents 2-furylmethoxy, 2-thienylmethoxy, 2-pyrrolyl-methoxy, —NR$^{16}$R$^{17}$ or —SO$_2$—NR$^{16}$R$^{17}$.

$R^{13}$ very particularly preferably represents hydrogen or carboxyl.

$R^{14}$ very particularly preferably represents hydrogen, acetyl, chloroacetyl or benzoyl.

$R^{15}$ very particularly preferably represents hydrogen.

$R^{14}$ and $R^{15}$, together with the linking nitrogen atom, also very particularly preferably represent 2-oxo-pyrrolidin-1-yl, 2-oxo-piperidin-1-yl, 2-oxo-azepan-1-yl, succinimino, maleinimino, dimethylmaleinimino, glutarimino, phthalimino, tetrafluorophthalimino, 4,5-dichlorophthalimino or tetrachlorophthalimino.

$R^{16}$ very particularly preferably represents hydrogen, methyl, ethyl, n-propyl, isopropyl, 2-chloroethyl, 2-bromoethyl, 2-chloro-1-propyl, 2-hydroxyethyl, 2-methoxyethyl, 2-furylmethyl, 2-thienylmethyl, 2-pyrrolylmethyl, 2-imidazolylmethyl, formyl, acetyl, propionyl, benzyl, 2-chlorobenzyl, 4-chlorobenzyl, benzoyl, 2-chlorobenzoyl, 4-chlorobenzoyl or 4-nitrobenzoyl or represents the radicals (a) to (l):

(a)
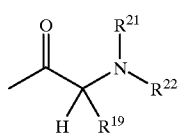

(b)
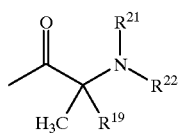

(c)
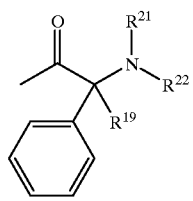

(d)
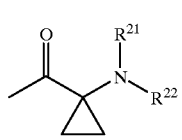

(e)
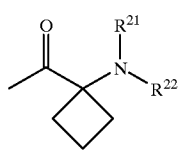

(f)
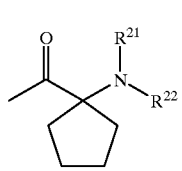

(g)
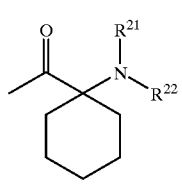

(h)
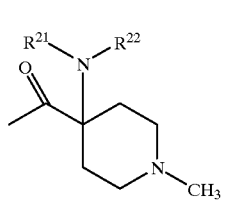

(i)
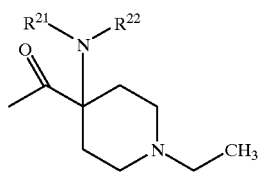

(j)
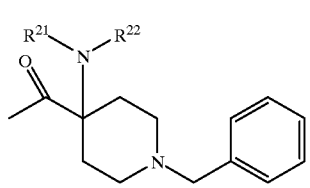

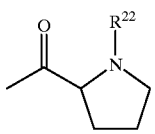
(k)

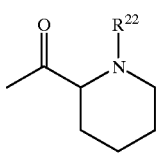
(l)

$R^{17}$ very particularly preferably represents hydrogen or, depending on $R^{16}$, an identical radical from the group: methyl, ethyl, n-propyl, isopropyl, 2-chloroethyl, 2-bromoethyl, 2-chloro-1-propyl, 2-hydroxyethyl, 2-methoxyethyl, 2-furylmethyl, 2-thienylmethyl, 2-pyrrolylmethyl, 2-imidazolylmethyl, benzyl, 2-chlorobenzyl or 4-chlorobenzyl.

$R^{16}$ and $R^{17}$ together also very particularly preferably represent phthaloyl, 3-fluorophthaloyl, 3,4-difluorophthaloyl, 4,5-difluorophthaloyl, 3,6-difluorophthaloyl, tetrafluorophthaloyl, 3-chlorophthaloyl, 4,5-dichlorophthaloyl, tetrachlorophthaloyl, 4-nitrophthaloyl, 3-methylphthaloyl, 4-methylphthaloyl, tetramethylphthaloyl, 4-tert-butylphthaloyl or, together with the linking nitrogen atom, represent an optionally fluorine-, chlorine-, methyl-, ethyl-, n-propyl-, isopropyl-, methoxy- or ethoxy-substituted and optionally n-acetylated monocyclic heterocycle having 5 to 8 ring members or bicyclic heterocycle having 7 to 11 ring members which is optionally bridged, optionally condensed with one or two carbocyclic ring systems, saturated or unsaturated and may contain 1 to 2 further hetero atoms from the group consisting of 1 or 2 nitrogen atoms, 1 oxygen atom and 1 sulfur atom, such as, in particular, morpholinyl, pyrrolyl or piperazinyl.

$R^{19}$ very particularly preferably represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl.

$R^{21}$ very particularly preferably represents hydrogen or methyl.

$R^{22}$ very particularly preferably represents hydrogen or a protective group known from peptide chemistry, such as acetyl, tert-butoxycarbonyl, benzyloxycarbonyl or benzyl.

Groups of the compounds of the formula (I) which are preferred according to the invention are the compounds of the formulae (I-a) to (I-d)

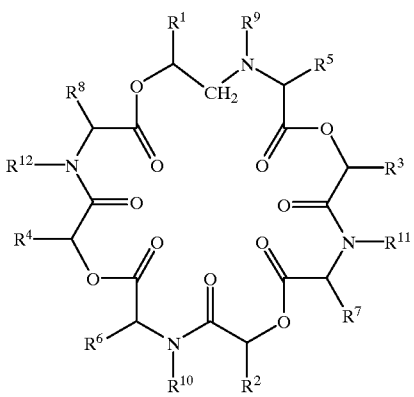
(I-a)

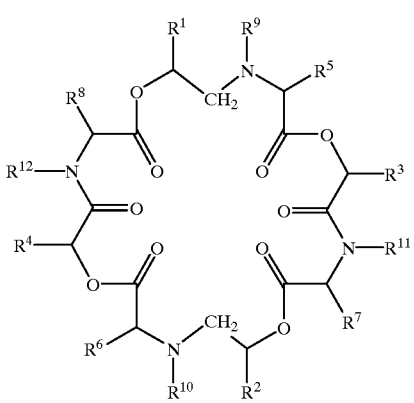
(I-b)

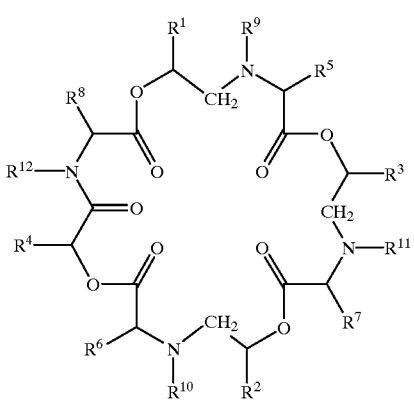
(I-c)

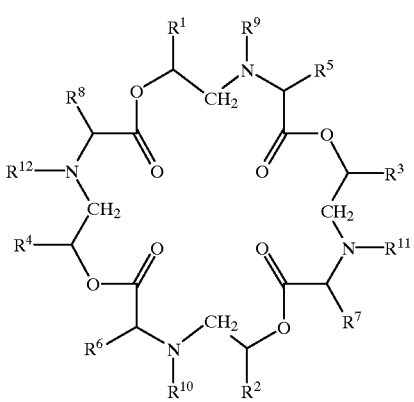
(I-d)

Groups of compounds of the formula (I) which are likewise preferred according to the invention are the compounds of the formula (I-1)

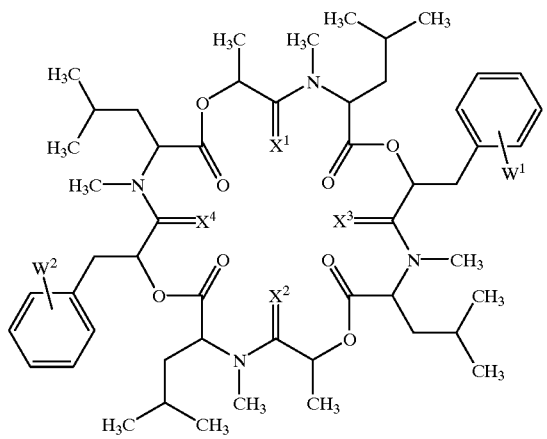
(I-1)

in which

C=X$^1$, C=X$^2$, C=X$^3$ and C=X$^4$ independently of one another are each as defined further above and W$^1$ and W$^2$ independently of one another each represent hydrogen or one of the radicals W.

Groups of compounds of the formula (I) which are very particularly preferred according to the invention are the compounds of the formulae (I-1-1), (I-1-2) and (I-1-4)

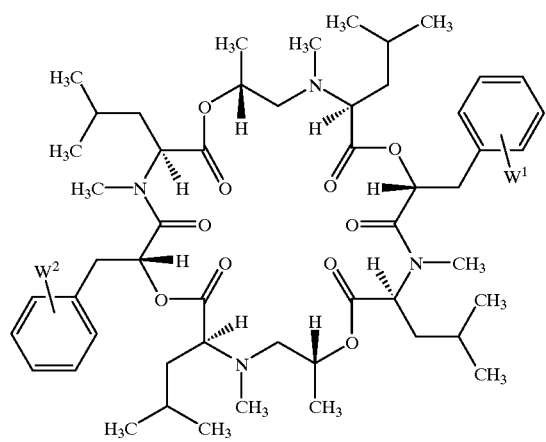
(I-1-1)

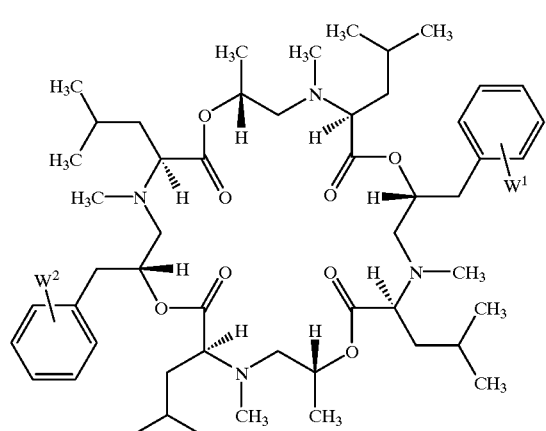
(I-1-2)

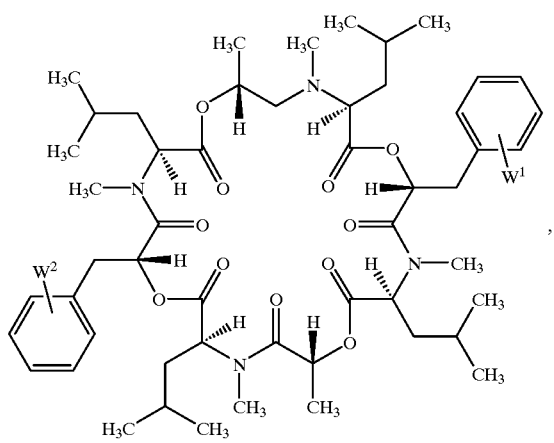
(I-1-4)

in which

W$^1$ and W$^2$ independently of one another each represent hydrogen or one of the radicals W.

Preferably, W$^1$ and W$^2$ represent the same radical.

The abovementioned general or preferred radical definitions or illustrations can be combined with one another as desired, that is to say combinations between the respective ranges and preferred ranges are also possible. They apply both to the end products and, correspondingly, to precursors and intermediates.

Preference according to the invention is given to those compounds of the formula (I) which contain a combination of the definitions listed above as being preferred (preferable).

Particular preference according to the invention is given to those compounds of the formula (I) which contain a combination of the definitions listed above as being particularly preferred.

Very particular preference according to the invention is given to those compounds of the formula (I) which contain a combination of the definitions listed above as being very particularly preferred.

Saturated or unsaturated hydrocarbon radicals such as alkyl or alkenyl, also in combination with hetero atoms, such as, for example, in alkoxy, may in each case, as far as this is possible, be straight-chain or branched.

Optionally substituted radicals may be mono- or polysubstituted, and the substituents in the case of polysubstitutions may be identical or different.

The terms heterocyclyl or hetaryl include, in addition to simple heterocyclic ring systems, also those which are condensed with carbocyclic ring systems.

If, for example, PF 1022A [cf. for example J. Antibiot. 45, 692 (1992)] is reacted with a boron hydride/tetrahydrofuran complex to prepare the compounds according to the invention, the course of the reaction in the process (a) according to the invention can be represented by the following equation:

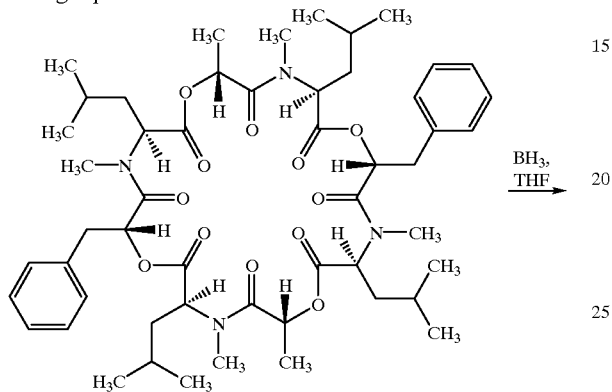

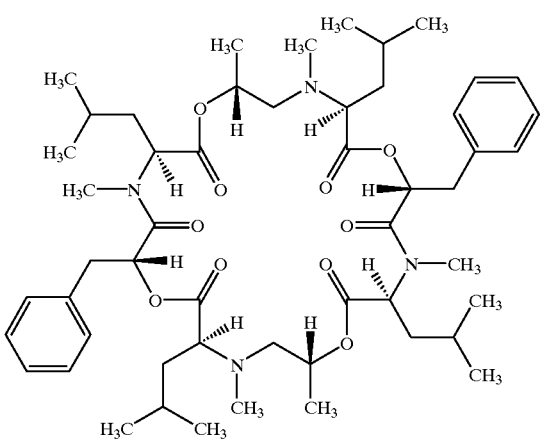

If, for example, PF 1022A and [2,4-bis(4-methoxyphenyl)]-1,3,2,4-dithiadiphosphetane-2,4-disulfide (Lawesson's reagent) are employed as starting materials and, in a second reaction step, reacted with sodium borohydride in the presence of nickel chloride, the course of the reaction in the process (b) according to the invention can be represented by the following equation:

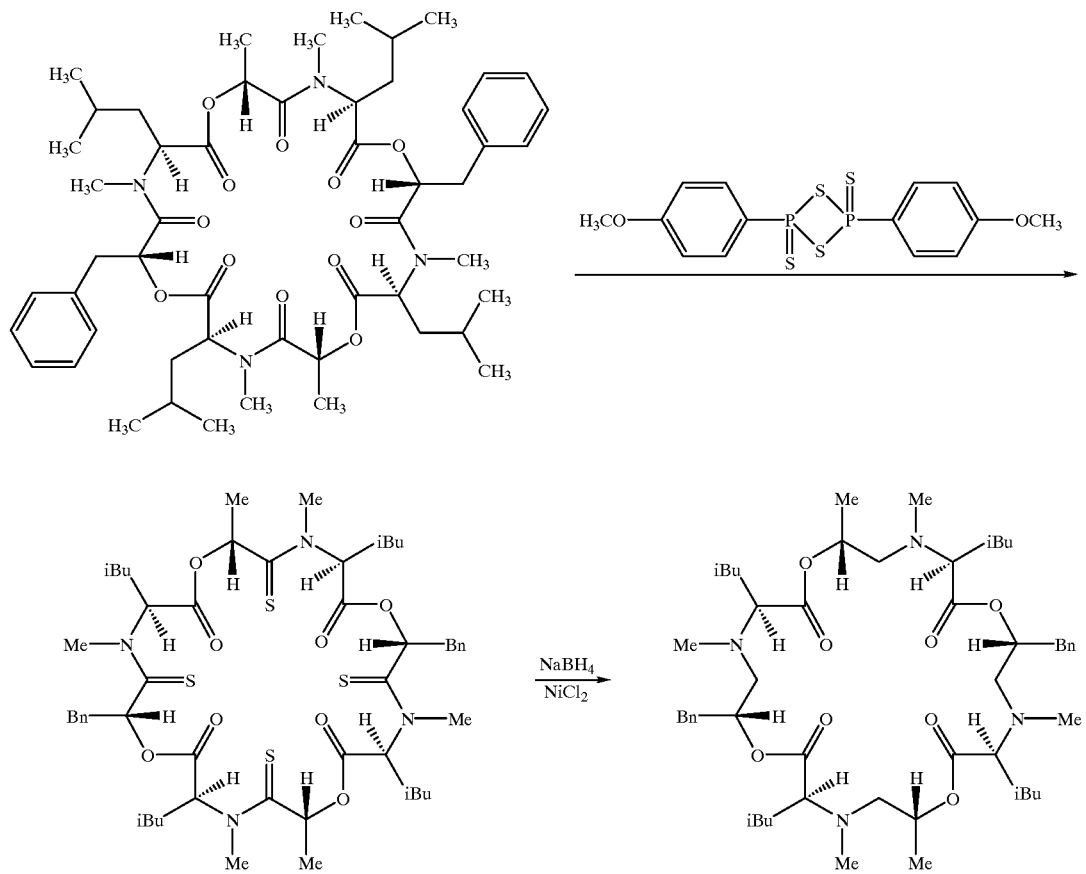

For a further derivatization of the compounds according to the invention, for example PF 1022A which is four-fold reduced is reacted with fuming nitric acid. The course of the reaction can be represented by the following equation:

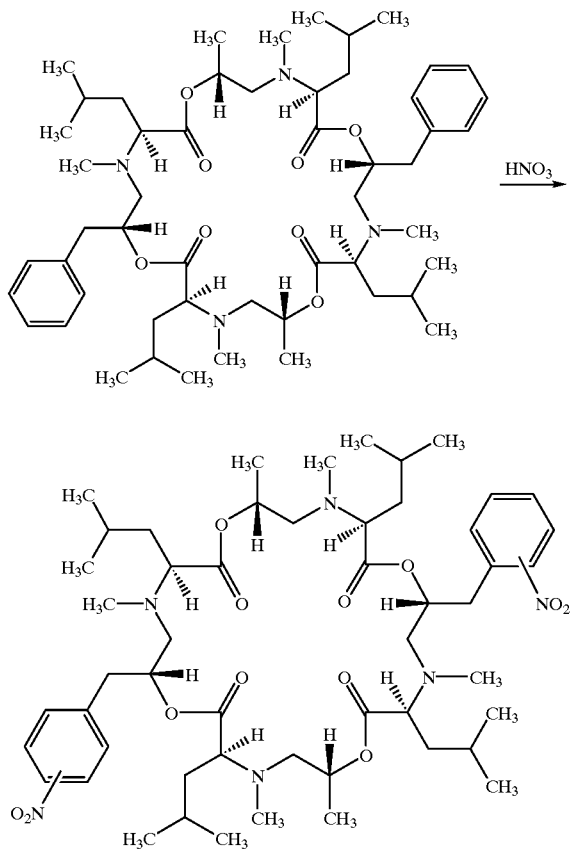

The cyclodepsipeptides required for carrying out the processes (a) and (b) according to the invention are known or can be prepared by fermentation and/or synthetically by known methods (cf., for example, EP 382 173 A2, JP 05 229997 A (cited in Derwent AN: 93-317424/40), EP 626 376 A1, EP 634 408 A1, EP 718 293 A1).

The borane furthermore required for carrying out the process (a) can be employed as diborane or as a borane complex such as borane-tetrahydrofuran or borane-dimethyl sulfide (cf. J. Org. Chem. 38, 912 (1973)).

The sulfurizing agent which is, if appropriate, required for carrying out the process (b) is a thionylation reagent, such as, for example, phosphorus pentasulfide or [2,4-bis(4-methoxyphenyl)]-1,3,2,4-dithiadiphosphetane-2,4-dithione (Lawesson's reagent).

The complex hydrides furthermore required, if appropriate, for carrying out the process (b) are, for example, sodium boronates such as sodium borohydride or sodium cyanoborohydride or lithium alanates such as lithium aluminum hydride.

Further derivatization of the compounds according to the invention is carried out, for example, by the following reactions: alkylation at one or more of the 4 ring nitrogen atoms, nucleophilic or electrophilic aromatic substitution at aromatic radicals, derivatizations of substituents of the aromatic radicals. Aromatic radicals are preferably understood as phenyl or benzyl which, in the formula (I), represent $R^3$ and $R^4$. Particularly preferably, this refers to the introduction, substitution or derivatization of at least one radical $W^1$ and $W^2$ other than hydrogen in compounds of the formula (I-1).

Compounds of the formula (I) according to the invention which are employed for alkylation are those in which at least one of the radicals $R^9$, $R^{11}$, $R^{10}$, $R^{12}$ represents hydrogen and the other radicals and groups have the abovementioned meanings and preferred meanings.

Preference is also given to using compounds of the formula (I) in which at least one of the radicals $R^3$, $R^4$, $R^5$, $R^6$, $R^7$, $R^8$ represents optionally substituted phenyl or benzyl for alkylation. For alkylation, these phenyl or benzyl radicals are substituted by at least one OH—, $NH_2$—, $NHR^{16}$— or SH group.

Suitable for use as alkylating agents are the alkylating agents which are customary in organic synthesis such as dialkyl sulfate, in particular $C_{1-4}$-dialkyl sulfate, optionally substituted alkyl halide, in particular $C_{1-4}$-alkyl halide, alkyl tosylate, in particular $C_{1-4}$-alkyl tosylate, alkyl mesylate in particular $C_{1-4}$-alkyl mesylate.

The alkylation is carried out under the conditions which are customary in organic synthesis (see also the processes described in EP-A 634 408).

Acylations of the OH—, $NH_2$—, $NHR^{16}$ or SH group can be carried out in a customary manner using
1. Acyl chlorides or carboxylic anhydrides, if appropriate in the presence of bases and solvents
2. Amino acids, which are optionally activated as amino acid fluorides or by coupling with coupling reagents known from peptide chemistry. In these cases, the amino group is protected in a customary manner by protective groups such as, for example, acetyl, t-butyloxycarbonyl or benzyloxycarbonyl. The amino acids can be employed in the form of their racemates or their pure enantiomers (D- or L-form). Preference is given to the L-form of the natural amino acids.

Such amino acids are, for example, amino acids of the formula

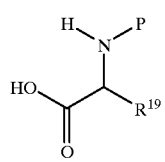

in which

P represents H or the radical of customary protective groups (for example acetyl, Boc, $Cb_z$), and $R^{19}$ represents one of the following radicals:
—$CH_3$,
—$CH_2CH(CH_3)_2$,
—$(CH_2)_4CH_3$,
—$CH(CH_3)_2$,
—$(CH_2)_2CH_3$,
—$C(CH_3)_3$,
—$CH_2Ph$,
—Ph,
—$(CH_2)_2$—OH,
—$CH(OH)CH_3$,
—$(CH_2)_2SCH_3$,
—$(CH_2)_2CONH_2$,

—CH₂—CO₂H,

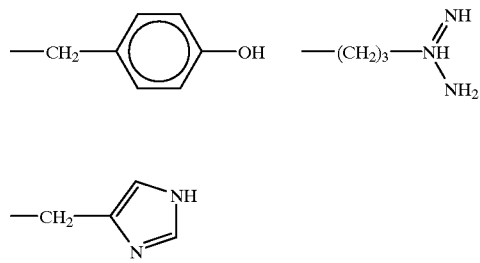

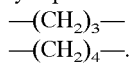

In the above formula for amino acids, P and $R_{19}$ together may represent one of the following divalent radicals
—(CH₂)₃—
—(CH₂)₄—.

Nucleophilic aromatic substitution preferably means the substitution of fluorine, chlorine, bromine, iodine, nitro by halides, alkoxides or primary or secondary amines or metal amides thereof. Furthermore, the term also includes the substitution of diazo groups, including, depending on reaction conditions and nucleophile, even radical substitution. Examples include the diazotization and subsequent hydrolysis in aqueous acid to give the phenol derivative or, using sulfur nucleophiles, to give the thiophenol derivative or sufide, undiluted in the presence of fluoride or tetrafluoroborate as nucleophile (Balz—Schiemann reaction), and under Sandmeyer conditions, for example using copper(I) halides or cyanide.

The nucleophilic aromatic substitution is preferably carried out using compuonds of the formula (I) according to the invention in which at least one of the radicals $R^3$, $R^4$, $R^5$, $R^6$, $R^7$, $R^8$ represents substituted phenyl or benzyl.

For nucleophilic substitution, these phenyl or benzyl radicals are substituted by fluorine, chlorine, bromine, iodine or nitro. They are preferably reacted with optionally substituted $C_{1-4}$-alkoxides or primary or secondary amines of the formula $HNR^{16}R^{17}$ in which $R^{16}$ and $R^{17}$ are each as defined above, or with metal amides.

The reaction is carried out by generally known methods of organic chemistry.

The diazotization and subsequent hydrolysis to give the corresponding phenols, thiophenols or sulfides and reactions of the type of the Balz-Schiemann or Sandmeyer reaction are carried out using compounds of the formula (I) in which at least one of the radicals $R^3$ to $R^8$ represents optionally substituted phenyl or benzyl, where at least one of these phenyl or benzyl radicals is substituted by amino. Such compounds are obtained according to the process described, for example, in EP-A 634 408, by nitration of the unsubstituted compounds and subsequent reduction of the nitro group to give the amino group.

Electrophilic aromatic substitution preferably means nitration, amidoalkylation, sulfurization, sulfochlorination, sulfonylation, bromination, iodination, Friedel-Crafts acylation and Friedel-Crafts alkylation.

The electrophilic aromatic substitution is carried out using compounds of the formula (I) in which at least one of the radicals $R^3$ to $R^8$ represents phenyl or benzyl. The practice of these substitutions is described, for example, in EP-A 634 408 and WO 95/3926. The details given therein with regard to starting materials, reactions and reaction conditions are expressly referred to.

Further derivatization of substituents of the aromatic radicals is carried out by reactions and under reaction conditions which are known from organic chemistry. Examples include: palladium-catalyzed alkenylation and alkynylation, reduction of a nitro group to give an amino group, alkylation of an amino group, in particular monoalkylation using a bifunctional alkylating reagent, followed by intramolecular alkylation to give a heterocyclic radical of the formula —$NR^{16}R^{17}$, alkylation of a hydroxyl group, oxidation of an alkylthio group to give the sulfoxide or sulfone.

The active compounds are suitable for controlling pathogenic endoparasites encountered in humans and in animal husbandry and livestock breeding, in productive livestock, breeding stock, zoo animals, laboratory animals, animals used in experiments, and pets, and have low toxicity toward warm-blooded animals. They are active against resistant and normally sensitive species and against all or some stages of development of the pests. By controlling the pathogenic endoparasites, it is intended to reduce disease, mortality and decreasing performance (for example in the production of meat, milk, wool, hides, eggs, honey, etc.), so that more economical and simpler animal keeping is possible by using the active compounds. The pathogenic endoparasites include Cestodes, Trematodes, Nematodes, in particular:

From the order of the Pseudophyllidea, for example Diphyllobothrium spp., Spirometra spp., Schistocephalus spp., Ligula spp., Bothridium spp., Diphlogonoporus spp.

From the order of the Cyclophyllidea, for example Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydratigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example Gyrodactylus spp., Dactylogyrus spp., Polystoma spp.

From the subclass of the Digenea, for example Diplostomum spp., Posthodiplostomum spp., Schistosoma spp., Trichobilharzia spp., Omithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhloccelum spp., Paramphistomum spp., Calicophoron spp, Cotylophoron spp., Gigantocotyle spp., Fischoederius spp., Gastrothylacus spp., Notocotylus spp., Catatropis spp., Plagiorchis spp., Prosthogonismus spp., Dicrocoelium spp., Collyriclum spp., Nanophyetus spp., Opisthorchis spp., Clonorchis spp., Metorchis spp., Heterophyes spp., Metagonimus spp.

From the order of the Enoplida, for example Trichuris spp., Capillaria spp., Trichlomosoides spp., Trichinella spp.

From the order of the Rhabditida, for example Micronema spp., Strongyloides spp. From the order of the Strongylida, for example Stronylus spp., Triodontophorus spp., Oesophagodontus spp., Trichonema spp., Gyalocephalus spp., Cylindropharynx spp., Poteriostromum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., Protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example Oxyuris spp., Enterobius spp., Passalurus spp., Syphacia spp., Aspiculuris spp., Heterakis spp.

From the order of the Ascaridia, for example Ascaris spp., Toxascaris spp., Toxocara spp., Parascaris spp., Anisakis spp., Ascaridia spp.

From the order of the Spirurida, for example Gnathostoma spp., Physaloptera spp., Thelazia spp., Gongylonema spp., Habronema spp., Parabronema spp., Draschia spp., Dracunculus spp.

From the order of the Filariida, for example Stephanofilaria spp., Parafilaria spp., Setaria spp., Loa spp., Dirofilaria spp., Litomosoides spp., Brugia spp., Wuchereria spp., Onchocerca spp.

From the group of the Gigantorhynchida, for example Filicollis spp., Moniliformis spp., Macracanthorhynchus spp., Prosthenorchis spp The active compounds according to the invention have, for example, outstanding activity against worms such as *Haemonchus contortus*.

The livestock and breeding stock include mammals, such as, for example, cattle, horses, sheep, pigs, goats, camels, water buffalo, donkeys, rabbits, fallow deer, reindeer, furbearing animals, such as, for example, minks, chinchilla or racoon, birds, such as, for example chickens, geese, turkeys or ducks, freshwater fish and sea fish, such as, for example, trout, carp and eels, reptiles and insects, such as, for example, honeybee and silkworm.

The laboratory and test animals include mice, rats, guinea pigs, golden hamsters, dogs and cats.

The pets include dogs and cats.

Administration can be effected prophylactically as well as therapeutically.

The active substances are administered, either directly or in the form of suitable preparations, enterally, parenterally, dermally, nasally, by treating the habitat or with the aid of shaped articles containing the active compound, such as, for example, strips, plates, tapes, collars, ear tags, limb bands or marking devices.

Enteral administration of the active compounds is effected for example orally in the form of powders, suppositories, tablets, capsules, pastes, drinks, granules, solutions, suspensions and emulsions which can be applied orally, boluses, medicated feed or drinking water. Dermal application is effected, for example, in the form of dipping, spraying, bathing, washing, pouring-on and spotting-on, and powdering. Parenteral administration is effected, for example, in the form of injection (intramuscular, subcutaneous, intravenous or intraperitoneal) or by implants.

Suitable preparations include:

Solutions, such as solutions for injection, oral solutions, concentrates for oral administration after dilution, solutions for use on the skin or in body cavities, pour-on formulations, gels;

Emulsions and suspensions for oral or dermal administration and for injection; semisolid preparations;

Formulations in which the active compound is incorporated in a cream base or in an oil-in-water or water-in-oil emulsion base;

Solid preparations, such as powders, premixes or concentrates, granules, pellets, tablets, boluses, capsules; aerosols and inhalants, shaped articles containing the active compound.

Solutions for injection are administered intravenously, intramuscularly and subcutaneously.

Solutions for injection are prepared by dissolving the active compound in a suitable solvent and, if desired, adding additives, such as solubilizers, acids, bases, buffer salts, antioxidants, or preservatives. The solutions are sterile-filtered and decanted into containers.

Suitable solvents include: physiologically acceptable solvents, such as water, alcohols, such as ethanol, butanol, benzyl alcohol, glycerol, hydrocarbons, propylene glycol, polyethylene glycols and N-methylpyrrolidone, and their mixtures.

If appropriate, the active compounds can also be dissolved in physiologically acceptable vegetable or synthetic oils which are suitable for injection.

Suitable solubilizers include: solvents which facilitate the dissolution of the active compound in the main solvent or which prevent precipitation of the active compound. Examples of solubilizers are polyvinylpyrrolidone, polyethoxylated castor oil and polyethoxylated sorbitan esters.

The following are preservatives: benzyl alcohol, trichlorobutanol, p-hydroxybenzoic esters or n-butanol.

Oral solutions are administered directly. Concentrates are first diluted to the administration concentration and then administered orally. Oral solutions and concentrates are prepared as described above in the case of the solutions for injection, sterile procedures not being necessary.

Solutions for use on the skin are applied drop by drop, smoothed on, rubbed in, splashed on or sprayed on, or applied by dipping, bathing or washing. These solutions are prepared as described above in the case of the solutions for injection.

It may be advantageous to add thickeners in the preparation process.

The following are thickeners: inorganic thickeners, such as bentonites, colloidal silica, aluminum monostearate, or organic thickeners, such as cellulose derivatives, polyvinyl alcohols and their copolymers, acrylates and methacrylates.

Gels are applied to the skin or smoothed on or introduced into body cavities. Gels are prepared by adding such an amount of thickener to solutions which have been prepared as described for the solutions for injection that a clear composition is formed which has an ointment-like consistency. The thickeners used are the thickeners indicated further above.

Pour-on and spot-on formulations are poured or splashed onto limited areas of the skin, the active compound penetrating the skin and acting systemically or distributing itself over the surface of the body.

Pour-on and spot-on formulations are prepared by dissolving, suspending or emulsifying the active compound in suitable solvents or solvent mixtures which are tolerated by the skin. If appropriate, other auxiliaries, such as colorants, absorption promoters, antioxidants, photostabilizers or tackifiers are added.

Suitable solvents include: water, alkanols, glycols, polyethylene glycols, polypropylene glycols, glycerol, aromatic alcohols, such as benzyl alcohol, phenylethanol or phenoxyethanol, esters, such as ethyl acetate, butyl acetate or benzyl benzoate, ethers, such as alkylene glycol alkyl ethers, such as dipropylene glycol monomethyl ether or diethylene glycol mono-butyl ether, ketones, such as acetone or methyl ethyl ketone, aromatic and/or aliphatic hydrocarbons, vegetable or synthetic oils, DMF, dimethyl acetamide, N-methylpyrrolidone, or 2,2-dimethyl-4-oxymethylene-1,3-dioxolane.

Colorants are all colorants which can be dissolved or suspended and which are approved for use in animals.

Examples of bioabsorption promoters are DMSO, spreading oils, such as isopropyl myristate, dipropylene glycol pelargonate, silicone oils, fatty acid esters, triglycerides or fatty alcohols.

The following are antioxidants: sulfites or metabisulfites, such as potassium metabisulfite, ascorbic acid, butylhydroxytoluene, butylhydroxyanisole or tocopherol.

Example of photostabilizers are substances from the class of the benzophenones or novantisolic acid.

Tackifiers are, for example, cellulose derivatives, starch derivatives, polyacrylates or natural polymers such as alginates or gelatin.

Emulsions can be administered orally, dermally or as injections.

Emulsions are either the water-in-oil type or the oil-in-water type.

They are prepared by dissolving the active compound either in the hydrophobic or in the hydrophilic phase and by homogenizing this phase with the solvent of the other phase, with the aid of suitable emulsifiers and, if appropriate, other auxiliaries, such as colorants, bioabsorption promoters, preservatives, antioxidants, photostabilizers, and viscosity-increasing substances.

Suitable hydrophobic phases (oils) include: paraffin oils, silicone oils, natural vegetable oils such as sesame seed oil, almond oil or castor oil, synthetic triglycerides, such as caprylic/capric acid biglyceride, a triglyceride mixture with vegetable fatty acids of chain length $C_{8-12}$ or other specifically selected natural fatty acids, mixtures of partial glycerides of saturated or unsaturated fatty acids which may also contain hydroxyl groups, and mono- and diglycerides of the $C_8/C_{10}$-fatty acids.

Fatty acid esters, such as ethyl stearate, di-n-butyryl adipate, hexyl laurate, dipropylene glycol pelargonate, esters of a branched fatty acid having a medium chain length with saturated fatty alcohols of chain length $C_{16}$–$C_{18}$, isopropyl myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, waxy fatty acid esters such as artificial duck uropygial fat, dibutyl phthalate, diisopropyl adipate, ester mixtures related to the latter, etc.

Fatty alcohols, such as isotridecyl alcohol, 2-octyldodecanol, cetylstearyl alcohol or oleyl alcohol.

Fatty acids, such as, for example, oleic acid and its mixtures.

Suitable hydrophilic phases include:

water, alcohols, such as, for example, propylene glycol, glycerol, sorbitol and their mixtures.

Suitable emulsifiers include:

nonionic surfactants, for example polyethoxylated castor oil, polyethoxylated sorbitan monooleate, sorbitan monostearate, glycerol monostearate, polyoxyethyl stearate or alkylphenol polyglycol ethers;

ampholytic surfactants, such as disodium N-lauryl-β-iminodipropionate or lecithin;

anionic surfactants, such as Na lauryl sulfate, fatty alcohol ether sulfates, and the monoethanolamine salt of mono/dialkylpolyglycol ether orthophosphoric ester;

cationic surfactants, such as cetyltrimethylammonium chloride.

Other suitable auxiliaries include: substances which increase the viscosity and stabilize the emulsion, such as carboxymethylcellulose, methylcellulose and other cellulose and starch derivatives, polyacrylates, alginates, gelatin, gum arabic, polyvinyl-pyrrolidone, polyvinyl alcohol, methylvinyl ether/maleic anhydride copolymers, polyethylene glycols, waxes, colloidal silica, or mixtures of the listed substances.

Suspensions can be administered orally, dermally or as an injection. They are prepared by suspending the active compound in a liquid excipient, if appropriate with the addition of other auxiliaries, such as wetting agents, colorants, bioabsorption promoters, preservatives, antioxidants and photostabilizers.

Suitable liquid excipients include all homogeneous solvents and solvent mixtures.

Suitable wetting agents (dispersants) include the surfactants indicated further above.

Suitable other auxiliaries include those indicated further above.

Semi-solid preparations can be administered orally or dermally. They are only distinguished from the above-described suspensions and emulsions by their higher viscosity.

To prepare solid preparations, the active compound is mixed with suitable excipients, if appropriate with the addition of auxiliaries, and the mixture is formulated as desired.

Suitable excipients include all physiologically acceptable solid inert substances. Suitable for this purpose are inorganic and organic substances. Inorganic substances are, for example, common salt, carbonates, such as calcium carbonate, hydrogen carbonates, aluminum oxides, silicas, clays, precipitated or colloidal silica, and phosphates.

Organic substances are, for example, sugars, cellulose, foodstuffs and animal feeds, such as powdered milk, animal meals, cereal meals, coarse cereal meals and starches.

Auxiliaries are preservatives, antioxidants and colorants which have already been mentioned further above.

Other suitable auxiliaries are lubricants and glidants, such as, for example, magnesium stearate, stearic acid, talc, bentonites, disintegrants, such as starch or crosslinked polyvinylpyrrolidone, binders, such as, for example, starch, gelatin or linear polyvinylpyrrolidone, and dry binders, such as microcrystalline cellulose.

In the preparations, the active compounds can also be present in mixtures with synergists or other active compounds which are active against pathogenic endoparasites. Examples of such active compounds are L-2,3,5,6-tetrahydro-6-phenylimidazolethiazole, benzimidazole carbamates, praziquantel, pyrantel or febantel.

Ready-to-use preparations contain the active compound in concentrations of 10 ppm to 20% by weight, preferably from 0.1 to 10% by weight.

Preparations which are diluted before use contain the active compound in concentrations of 0.5 to 90% by weight, preferably from 5 to 50% by weight.

In general, it has been found to be advantageous to administer amounts of about 1 to 100 mg of active compound per kg of bodyweight per day to obtain effective results.

The preparation and the use of the active compounds according to the invention can be seen from the examples below.

PREPARATION EXAMPLES

Example 1

(Process a)

(I-b)

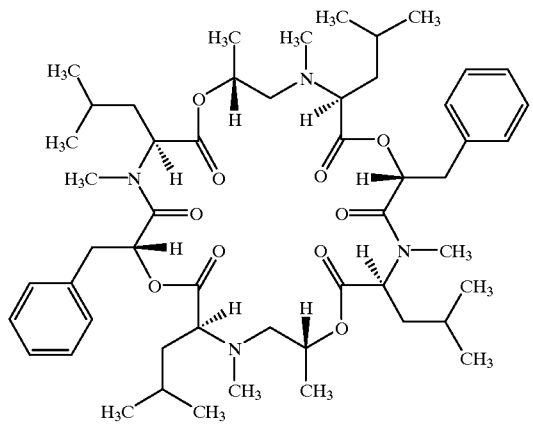

51 ml of a 1M solution of borane-THF complex in THF were quickly added in a dropwise manner to a solution of 14.25 g (15 mmol) of 8,20-dibenzyl-5,11,17,23-tetraisobutyl-2,4,10,14,16,22-hexamethyl-1,7,13,19-tetraoxa-4,10,16,22-tetraaza-cyclotetracosan-3,6,9,12,15,18,21,24-octaone (PF 1022) in 150 ml of dry tetrahydrofuran (THF). The solution was heated under reflux for 1 h. The mixture was subsequently cooled in an ice-bath and hydrolyzed by addition of 13.35 g (150 mmol) of 2-amino-2-methylpropanol. The mixture was stirred for 30 min, semisaturated sodium chloride solution was then added and the mixture was extracted with ethyl acetate. The mixture was dried over sodium sulfate and concentrated and the product was purified by column chromatography (silica gel; cyclohexane; ethyl acetate=10:1) and crystallization from n-hexane/ethyl acetate. This gave 4.97 to 6.08 g (34 to 41% of theory) of the direduction product 8,20-dibenzyl-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (1-b) as a colorless solid of melting point 149 to 150° C.

MS(FAB): m/z (nominal mass): 921 (M+H$^+$); HR-MS: calc. for $C_{52}H_{80}N_4O_{10}Na$ 943,5772; found 943,5776.

From the other fractions and the mother liquor of the crystallization, the mono-, the tri- and the tetrareduction product were isolated by further column chromatography and crystallization.

Monoreduction product (1-a):

M.p.: 130 to 132° C.; MS (FAB): m/z (nominal mass): 935 (M+H$^+$), 957 (M+Na$^+$); HR-MS: calc. for $C_{52}H_{78}N_4O_{11}Na$ 957,5565; found 957,5565.

Trireduction product (1-c):

MS (FAB): m/z (nominal mass): 907 (M+H$^+$), 929 (M+Na$^+$).

Tetrareduction product (1-d)=(Ex. 2):

MS (FAB): m/z (nominal mass): 893 (M+H$^+$); 915 (M+Na$^+$).

Example 2

(Process a)

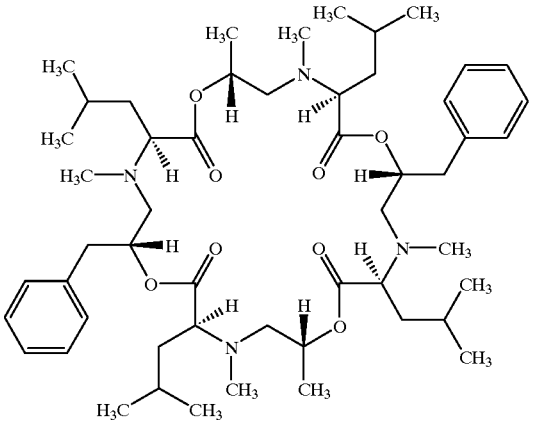

Similar to Example 1, 4.75 g (5 mmol) of PF 1022 in 10 ml of THF were reacted with 100 ml of a 1 M solution of borane and worked-up. Chromatography gave 0.75 g (17% of theory) of tetrareduction product 8,20-dibenzyl-5,11,17,23-tetraisobutyl-2,4,10,14,16,22-hexamethyl-1,7,13,19-tetraoxa-4,10,16,22-tetraazacyclotetracosan-6,12,18,24-tetraone as a light-yellow viscous oil.

MS (FAB): m/z (nominal mass): 893 (M+H$^+$); 915 (M+Na$^+$)

Example 3

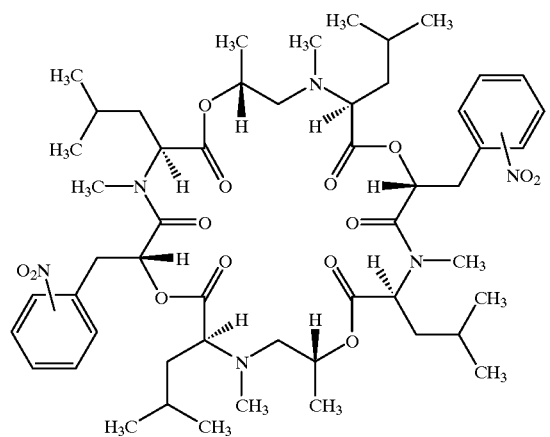

At –10° C., 2.68 g (2.91 mmol) of 8,20-dibenzyl-5,11,17,23-tetraisobutyl-2,4,10,14, -16,22-hexamethyl-1,7,13,19-tetraoxa-4,10,16,22-tetraaza-cyclotetracosan-6,9,12,18,-21,24-hexaone (for example according to Example 1) were introduced into fuming nitric acid. The mixture was stirred at 0° C. for 2 h, poured on ice and made basic using sodium carbonate. The aqueous phase was extracted three times with dichloromethane, the combined organic phases were dried over sodium sulfate and the solvent was evaporated to give 2.97 g (100% of theory) of a mixture of the regioisomeric 5,11,17,23-tetraisobutyl-2,4,10,14,16,22-hexamethyl-8,20-bis-(nitrobenzyl)-1,7,13,19-tetraoxa-4,10,16,22-tetraaza-cyclotetracosan-6,9,12,18,21,24-hexaones. The individual isomers can be separated by chromatography at the next reaction stage (hydrogenation, Ex. 4).

MS (MALDI): m/z (nominal mass): 1011 (M+H$^+$).

Example 4

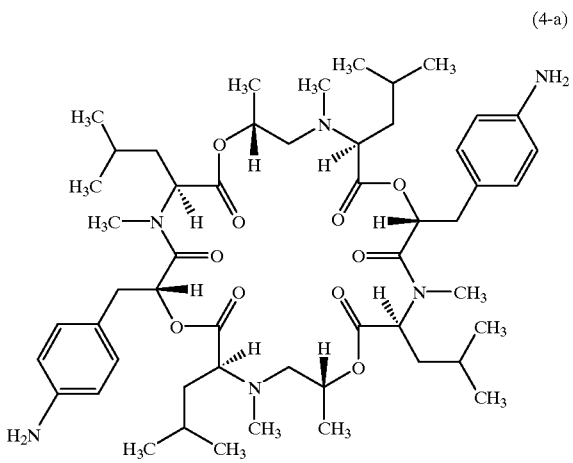

(4-a)

2.97 g (2.91 mmol) of 5,11,17,23-tetraisobutyl-2,4,10,14,16,22-hexamethyl-8,20-di-(4-nitrobenzyl)-1,7,13,19-tetraoxa-4,10,16,22-tetraaza-cyclotetracosan-6,9,12,18,21,24-hexaone (for example according to Example 3) were dissolved in a mixture of 40 ml of ethyl acetate and 8 ml of ethanol, admixed with 297 mg of palladium hydroxide on carbon (20% Pd) and hydrogenated at room temperature and under atmospheric pressure for 6 h. The catalyst was filtered off and rinsed with ethyl acetate. The filtrate was concentrated and chromatographed over silica gel using the eluent cyclohexane/ethyl acetate (2.5:1). This gave 1.52 g (54% of theory) of the isomeric 8,20-bis-(aminobenzyl)-5,11,17,23-tetraisobutyl-2,4,10,14,16,22-hexamethyl-1,7,13,19-tetraoxa-4,10,16,22-tetraazatetracosan-6,9,12,18,21,24-hexaones. MS (MALDI): m/z (nominal mass): 951 (M+H$^+$).

Preparative HPLC of the isomer mixture (mobile phase: acetonitrile/water=40:60+1 trifluoroacetic acid) gave 639 mg (23% of theory) of the bis-para product 8,20-bis-(4-aminobenzyl)-5,11,17,23-tetraisobutyl-2,4,10,14,16,22-hexamethyl-1,7,13,19-tetraoxa-4,10,16,22-tetraazatetracosan-6,9,12,18,21,24-hexaone (4-a), 307 mg (11%) of the ortho-para isomer (4-b) and 27 mg (1%) of the bis-ortho isomer.

Example 5

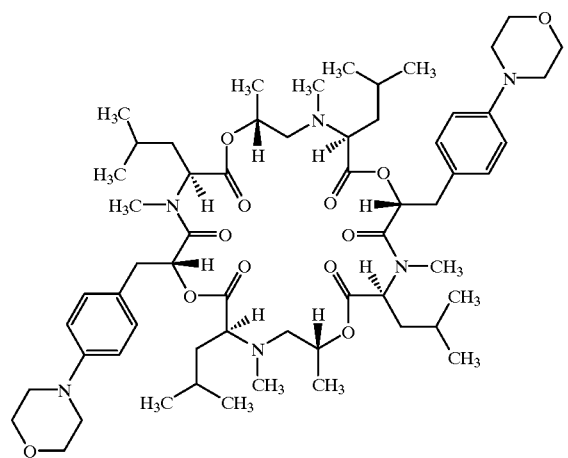

607 mg (0.638 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example according to Example 4, Compound 4-a), 529 mg (3.83 mmol) of potassium carbonate and 952 mg (6.38 mmol) of sodium iodide were initially charged in 10 ml of dimethylformamide (DMF), admixed at room temperature with 621.8 mg (2.68 mmol) of bis-(2-bromoethyl) ether and stirred at 30° C. for 20 h. The reaction mixture was concentrated under reduced pressure. The residue was taken up in water and extracted three times with dichloromethane. The combined extracts were dried over sodium sulfate and concentrated. Columnchromatographic purification (silica gel; cyclohexane: ethyl acetate=2:1) gave 453 mg (65% of theory) of 5,11,17,23-tetraisobutyl-2,4,10,14,16,22-hexamethyl-8,20-bis-[4-(N-morpholinyl)benzyl]-1,7,13,19-tetraoxa-4,10,16,22-tetraaza-cyclotetracosan-6,9,12,18,21,24-hexaone.

MS (MALDI): m/z (nominal mass): 1091 (M+H$^+$).

Example 6

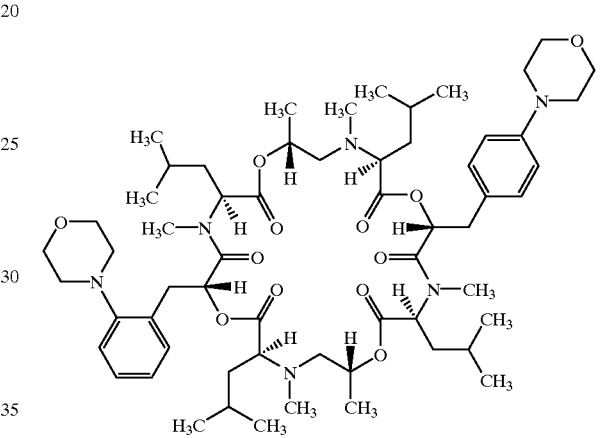

By the method of Example 5, 227.8 mg of 8-(4-aminobenzyl)-20-(2-aminobenzyl)-5,11,17,23-tetraisobutyl-2,4,10,14,16,22-hexamethyl-1,7,13,19-tetraoxa-4,10,16,22-tetraazatetracosan-6,9,12,18,21,24-hexaone (for example according to Example 4, Compound 4-b) gave 196 mg (75% of theory) of 5,11,17,23-tetraisobutyl-2,4,10,14,16,22-hexamethyl-8-[-4-(N-morpholinyl)benzyl]-20-[2-(N-morpholinyl)benzyl]-1,7,13,19-tetraoxa-4,10,16,22-tetraaza-cyclotetracosan-6,9,12,18,21,24-hexaone.

MS (MALDI): m/z (nominal mass): 1091 (M+H$^+$).

Example 7

(Process a)

223 mg (0.2 mmol) of 5,11,17,23-tetraisobutyl-2,4,10,14,16,22-hexamethyl-8,20-bis-[4-(N-morpholinyl)benzyl]-1,7,13,19-tetraoxa-4,10,16,22-tetraaza-cyclotetracosan-3,6,9,12,15,18,21,24-octaone (cf. EP 634 408 A1) were dissolved in 2 ml of dry THF. At room temperature, 2.16 ml of a 1M solution of borane-THF complex in THF were added. The solution was heated under reflux for 1.5 h and then cooled to 0° C. 249 mg (2.8 mmol) of 2-amino-2-methyl-1-propane in 2 ml of dry THF were added, and the solution was stirred for about 1 h. The reaction solution was taken up in methyl tert-butyl ether and washed with saturated sodium chloride solution. The solution was dried over sodium sulfate and concentrated and the crude product was then filtered through a small amount of silica gel (cyclohexane:ethyl acetate 1:1 to 1:3). The reduction products were isolated by preparative HPLC.

Direduction product 5,11,17,23-tetraisobutyl-2,4,10,14,16,22-hexamethyl-8,20-bis-[4-(N-morpholinyl)benzyl]-1,7,13,19-tetraoxa-4,10,16,22-tetraaza-cyclotetracosan-6,9,12,18,21,24-hexaone (7-b)=(Ex. 5): 37 mg MS (MALDI): m/z (nominal mass): 1091 (M+H$^+$), 1113 (M+Na$^+$).

Trireduction product 5,11,17,23-tetraisobutyl-2,4,10,14,16,22-hexamethyl-8,20-bis-[4-(N-morpholinyl)benzyl]-1,7,13,19-tetraoxa-4,10,16,22-tetraaza-cyclotetracosan-6,9,12,18,24-pentaone (7-c): 10 mg MS (MALDI): m/z (nominal mass): 1077 (M+H$^+$).

Tetrareduction product 5,11,17,23-tetraisobutyl-2,4,10,14,16,22-hexamethyl-8,20-bis-[4-(N-morpholinyl)benzyl]-1,7,13,19-tetraoxa-4,10,16,22-tetraaza-cyclotetracosan-6,12,18,24-tetraone (7-d): 22 mg MS (MALDI): m/z (nominal mass): 1063 (M+H$^+$); 1085 (M+Na$^+$).

Example 8

(Process a)

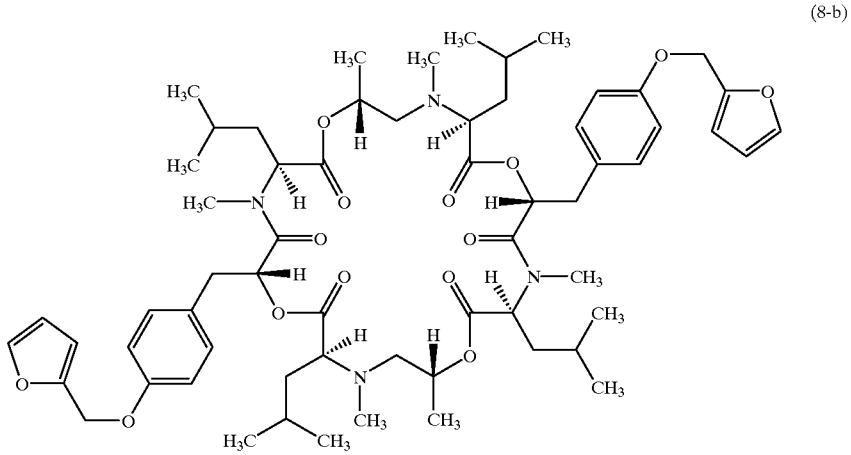

(8-b)

By the method of Example 1, 0.57 g (0.5 mmol) of 5,11,17,23-tetraisobutyl-2,4,10,14,16,22-hexamethyl-8,20-bis- [4-(2-furylmethoxy)benzyl]-1,7,13,19-tetraoxa-4,10,16,22-tetraaza-cyclotetracosan-3,6,9,12,15,18,21,24-octaone is reacted and worked up. This gave 245 mg (44% of theory) of direduction product 5,11,17,23-tetraisobutyl-2,4,10,14,16,22-hexamethyl-8,20-bis-[4-(2-furylmethoxy)benzyl]-1,7,13,19-tetraoxa-4,10,16,22-tetraaza-cyclotetracosan-6,9,12,18,21,24-hexaone (8-b) of melting point 116 to 119° C.

MS (ESI): m/z (nominal mass): 1113 (M+H$^+$), 1135 (M+Na$^+$).

In addition, 76 mg of monoreduction product and 32 mg of tetrareduction product were obtained.

Example 9

(Process a)

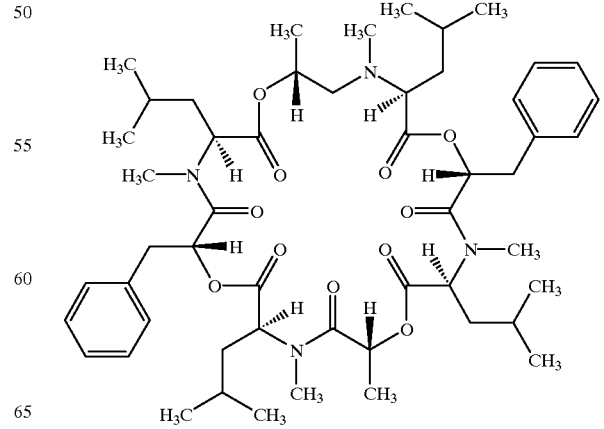

37.5 ml (37.5 mmol) of a 1M solution of borane-THF complex in THF were quickly added in a dropwise manner to a solution of 30.88 g (31.5 mmol) of PF 1022 in 190 ml of THF. The solution was heated under reflux for 2 h and subsequently cooled to 0° C. and hydrolyzed by addition of 30 ml of 2-amino-2-methylpropanol. Stirring was continued at room temperature for 45 min and semisaturated sodium chloride solution was added and the mixture was extracted 3× with ethyl acetate. The combined extracts were dried over magnesium sulfate and concentrated and the crude product was filtered through a glass fritt (Ø=10 cm) filled with silica gel, using cyclohexane/ethyl acetate (15:1 to 7:1). This gave 9.11 g (31% of theory) of 8,20-dibenzyl-5,11,17,23-tetraisobutyl-2,4,10,14,16,22-hexamethyl-1,7,13,19-tetraoxa-4,10,16,22-tetraaza-cyclotetracosan-6,9,12,15,18,21,24-heptaone (1-a) (cf. Ex. 1).

Example 10

(Process a)

By the method of Example 1, 2.99 g (3.25 mmol) of 8,20-dibenzyl-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (1-b) (for example from Ex. 1) in 20 ml of THF were reacted with 9.75 ml (9.75 mmol) of a 1M solution of borane. Column chromatography (silica gel, Ø=4.5 cm, l=25 cm; cyclohexane:ethyl acetate 50:1 to 5:1) gave 0.72 g of tetrareduction product 8,20-dibenzyl-5,11,17,23-tetraisobutyl-2,4,10,14,16,22-hexamethyl-1,7,13,19-tetraoxa-4,10,16,22-tetraaza-cyclotetracosan-6,12,18,24-tetraon (2) (cf. Ex. 2), 0.22 g of trireduction product (1-c) and 0.91 g of unreacted starting material.

Example 11

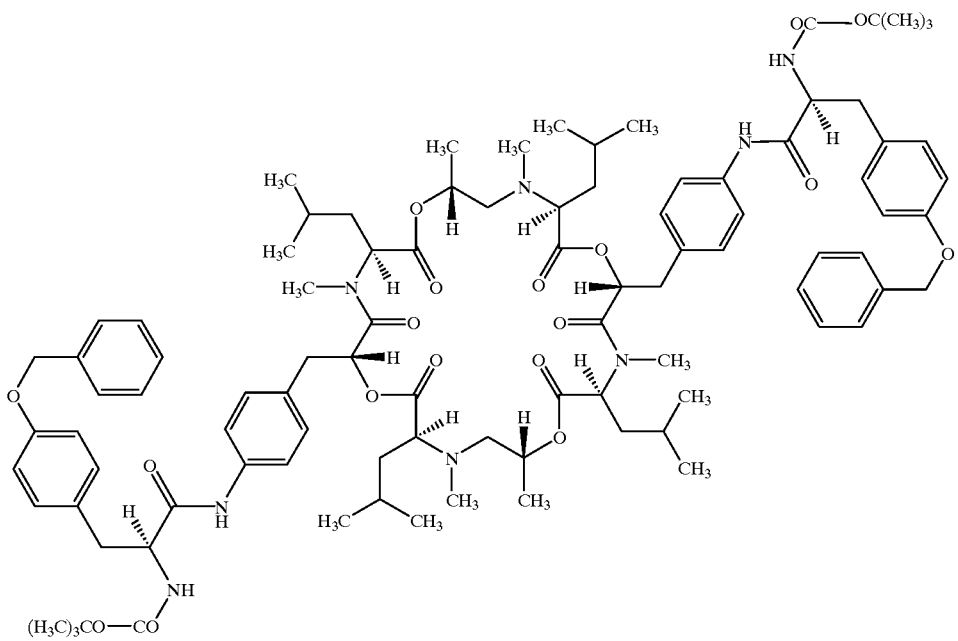

1.34 g (3.6 mmol) of O-benzyl-N-t-butoxycarbonyl-L-tyrosine were initially charged in 15 ml of acetonitrile, and 485.7 mg (4.8 mmol) of triethylamine and 520.9 mg (4.8 mmol) of ethyl chioroformate were added in succession. The mixture was stiffed at room temperature for 2 minutes, a solution of 1.43 g (1.5 mmol) of 8,20-bis-(4-amiinobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 4) in 3 ml of acetonitrile was added and the mixture was stirred at room temperature for 3–4 h. The reaction mixture was taken up in ethyl acetate, washed with semiconcentrated sodium chloride solution, dried and evaporated under reduced pressure. Column chromatography (Ø=4.5 cm, l=20 cm; cyclohexane:ethyl acetate 2:1) gave 1.81 g (73% of theory) of 8,20-bis-[4-β-(4-benzyloxyphenyl)-α-tert-butoxycarbonylamino-propionylamninobenzyl]-5, 11,1 7,23-tetraisobutyl-2,4,10,14,16,22-hexamethyl-1,7,13,19-tetraoxa-4,10,16,22-tetraaza-cyclotetracosan-6,9,12,18,21,24-hexaone.

MS (ESI): m/z (nominal mass): 1657 (M+H$^+$).

Example 12

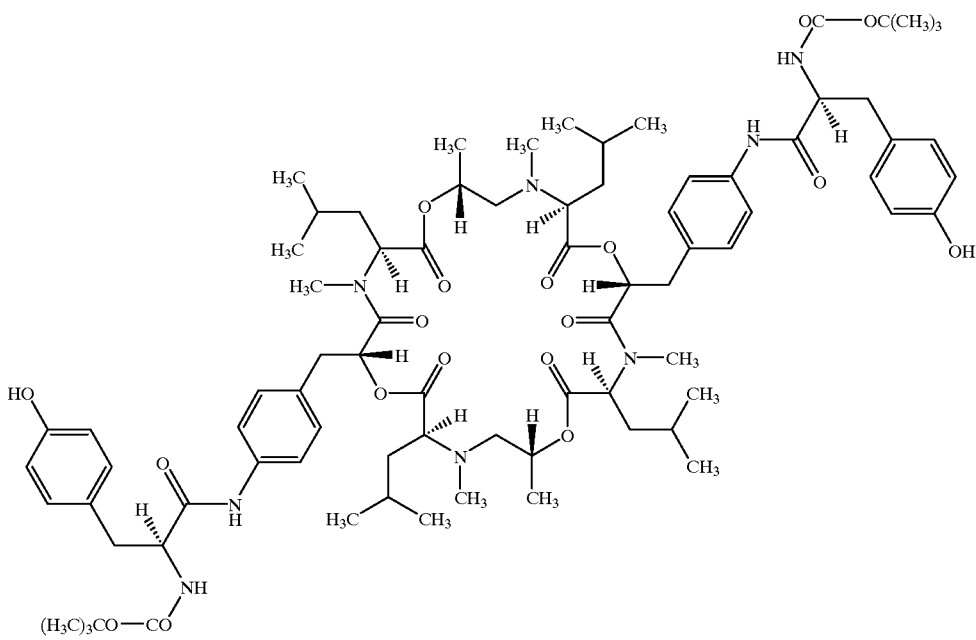

829.0 mg (0.50 mmol) of doubly protected tyrosine derivative from Example 12 and 83 mg of palladium/carbon (10%) catalyst were initially charged in 5 ml of ethyl acetate. The mixture was stirred in an atmosphere of hydrogen at room temperature and under atmospheric pressure. The reaction was checked by TLC, and in order to complete the hydrogenolysis, further catalyst and glacial acetic acid were added. The conversion was checked once more, the catalyst was filtered off through a filter aid (Celite®) and the filtrate was concentrated and purified by column chromatography (Ø=4.5 cm, l=10 cm; cyclohexane:ethyl acetate 2:1). This gave 0.52 g (70% of theory) of 8,20-bis-[4-α-tert-butoxycarbonylamino-β-(4-hydroxyphenyl)-propionylaminobenzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone.

MS (ESI): m/z (nominal mass): 1477 (M+H$^+$), 739 (M+2H$^{2+}$).

475.6 mg (0.50 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 4) were initially charged in 1.5 ml of glacial acetic acid and heated under reflux with 162.9 mg (1.1 mmol) of phthalic anhydride for 5 h. The mixture was concentrated, the residue was taken up in tertbutyl methyl ether (MTBE) and washed with sodium bicarbonate solution and saturated sodium chloride solution. The solution was dried with sodium sulfate, reconcentrated and subsequently filtered over a short silica gel column (Ø=3 cm, l=5 cm) using cyclohexane/ethyl acetate 2:1. Evaporation of the filtrate gave 0.55 g of slightly contaminated 8,20-bis-(4-phthalimidobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone as a yellow foam.

MS (ESI): m/z (nominal mass): 1211 (M+H$^+$), 1233 (M+Na$^+$).

Example 13

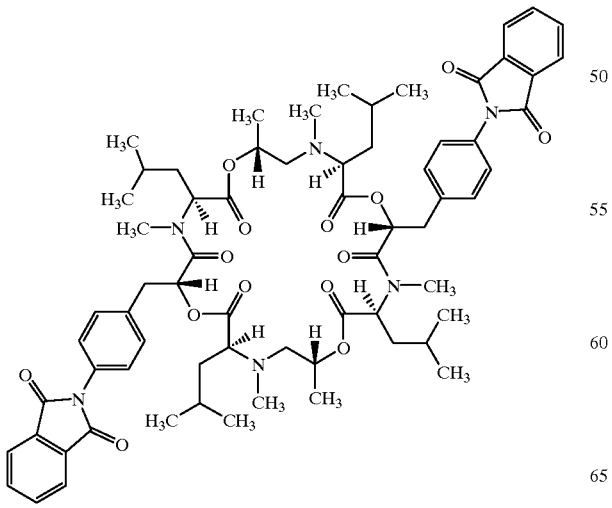

Example 14

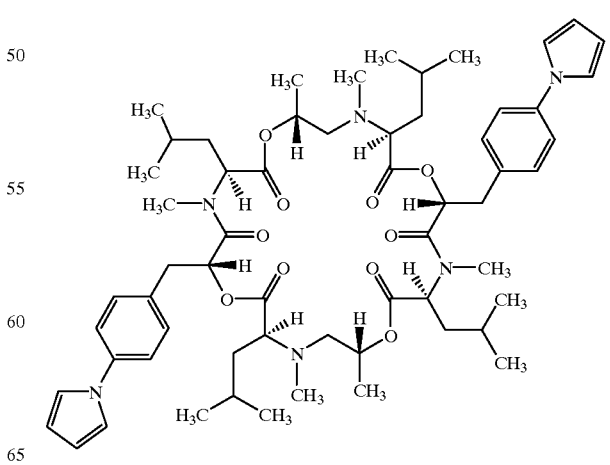

1.427 g (1.50 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 4) were initially charged in 7.5 ml of dry toluene, and 594.6 mg (582 µl; 4.5 mmol) of 2,5-dimethoxytetrahydrofuran were added. At 0° C., 851.7 mg (3.0 mmol) of phosphorus pentoxide were added and the mixture was stirred, initially at this temperature and then at room temperature. Since the conversion was incomplete (TLC check), the mixture was once more cooled to 0° C. and the same amounts of 2,5-dimethoxytetrahydrofuran and phosphorus pentoxide were added and allowed to react. For work-up, the mixture was admixed with water and extracted with ethyl acetate, and the combined extracts were dried and concentrated. To complete the extraction, the aqueous phase was subsequently shaken again with dichloromethane. The combined residues of the organic extracts were subsequently purified by column chromatography (Ø=4 cm, l=28 cm; cyclohexane:ethyl acetate 3:1). This gave 353.9 mg (22% of theory) 8,20-bis-[4-(1-pyrrolyl)-benzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone.

MS (ESI): m/z (nominal mass): 1051 (M+H$^+$), 1073 (M+Na$^+$).

Example 15

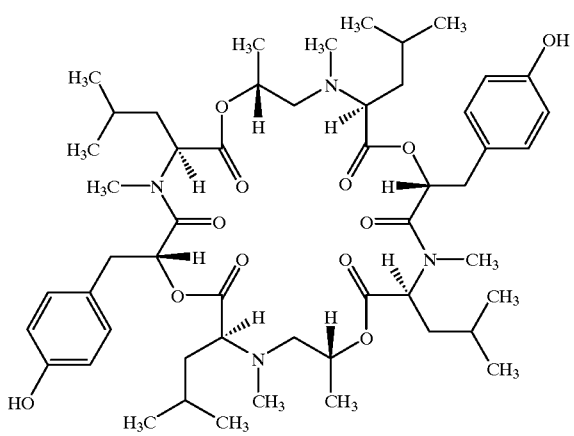

100 mg (0.1048 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 4) were dissolved in 1 ml of trifluoroacetic acid and admixed with 16.6 mg (0.24 mmol) of sodium nitrite. The mixture was heated to 60° C. and stirred for 1 h. The mixture was then concentrated under reduced pressure and, to remove residual acid, evaporated 3× under reduced pressure, in each case after the addition of dry toluene. The residue was taken up in 5 ml of dioxane, 1 ml of water and 175 mg of sodium carbonate were added and the mixture was stirred overnight. More water was added and the mixture was extracted with ethyl acetate. The combined extracts were dried, concentrated and filtered through a Pasteur pipette filled with silica gel using a mixture of cyclohexane/ethyl acetate (3:1). The crude product was purified over a semipreparative HPLC column (RP phase; acetonitrile/water). This gave 27.2 mg of 8,20-bis-(4-hydroxybenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone which was identified by mass spectroscopy and NMR spectroscopy ($^1$H, 500 MHz).

MS(MALDI): m/z (nominal mass): 953 (M+H$^+$), 975 (M+Na$^+$).

Example 16

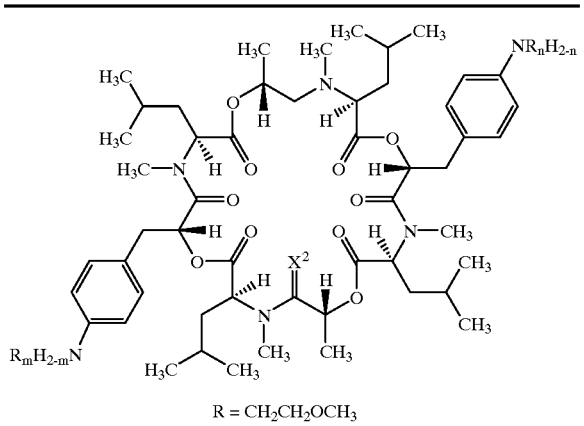

R = CH$_2$CH$_2$OCH$_3$

| Example No. | X$^2$ | n | m |
|---|---|---|---|
| 16-a | H$_2$ | 1 | 1 |
| 16-b | H$_2$ | 2 | 1 |
| 16-c, 17-b | H$_2$ | 2 | 2 |
| 17-a | O | m + n = 3 | |

871.9 mg (6.309 mmol) of potassium carbonate and 1.568 g (10.52 mmol) of sodium iodide were initially charged in 20 ml of DMF. 613 mg (415 µl; 4.41 mmol) of 1-bromo-2-methoxyethane and a solution of 1.00 g (1.052 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 4) in 5 ml of DMF were added and the mixture was heated to 80° C. and stirred for 20 h. A further 306 mg (2.20 mmol) of 1-bromo-2-methoxyethane were then added and allowed to react at 100° C. for 3 h. The mixture was cooled, taken up in water and extracted with dichloromethane. The combined filtrates were dried, concentrated and then separated by flash chromatography (column: Ø=4.5 cm, l=25 cm; silica gel; cyclohexane:ethyl acetate=2:1). The remainder (462.5 mg) left from 497 mg of evaporation residue of the middle main fraction was, after mass spectroscopic and NMR analysis, separated further over a semipreparative HPLC column (RP-phase; acetonitrile/water) using a number of runs. In order of elution, 204.9 mg of dialkylated compound 8,20-bis-(4-β-methoxyethylaminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (16-a), 151.2 mg of trialkylated compound 8-[4-bis-(β-methoxyethyl)aminobenzyl]-20-(4-β-methoxyethyl-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (16-b) and 24.8 mg of tetraalkylated compound 8,20-bis-[4-bis-(β-methoxyethyl)aminobenzyl]-5,11,17,23-tetraisobutyl-2,4,10,14,16,22-hexamethyl-1,7,13,19-tetraoxa-4,10,16,22-tetraazacyclotetracosan-6,9,12,18,21,24-hexaone (16-c) were obtained. The last fraction from the preparative chromatography (118 mg) contained predominantly trialkylated compound (16-b).

MS (MALDI): m/z (nominal masses): dialkylation product (16-a): 1067 (M+H$^+$), 1089 (M+Na$^+$), trialkylation product (16-a): 1125 (M+H$^+$), 1147 (M+Na$^+$), tetraalkylation product (16-a): 1183 (M+H$^+$).

Example 17

By the method of Example 16, a solution of 1.00 g (1.052 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone in 3 ml of DMF was allowed to react with 613 mg (415 µl; 4.41 mmol) of 1-bromo-2-methoxyethane in the presence of 435.9 mg (3.15 mmol) of potassium carbonate and 784.5 mg (5.26 mmol) of sodium iodide in 10 ml of DMF at 100° C. for 22 h. Subsequently, an identical amount of fresh 1-bromo-2-methoxyethane was added and the mixture was allowed to react at 100° C. for a further 6 h. After similar work-up and flash chromatography, 104 mg of 8(or 20)-[4-bis-(β-methoxyethyl)aminobenzyl]-20(or 8)-(4-β-methoxyethylaminobenzyl)-5,11,17,23-tetraisobutyl-2,4,10,14,16,22-hexamethyl-1,7,13,19-tetraoxa-4,10,16,22-tetraaza-cyclotetracosan-6,9,12,15,18,21,24-heptaone (17-a), 59.5 mg of intermediate fraction and 213.8 mg (34% of theory) of 8,20-bis-[4-bis-(β-methoxyethyl)aminobenzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (17-b)≡(16-c) were obtained, after a forerun of about 30mg. The formation of tetraone (17-a) is caused by the contamination of the starting material by (as compared to PF 1022) singly reduced diaminobenzyl derivative, which could be isolated. It was formed in the preceding synthesis sequence, because separation had not been carried out in a repetition of Example 1).

MS (MALDI): m/z (nominal mass):

Compound (17-a): 1139 (M+H$^+$), 1161 (M+Na$^+$), 1177 (M+K$^+$).

Example 18

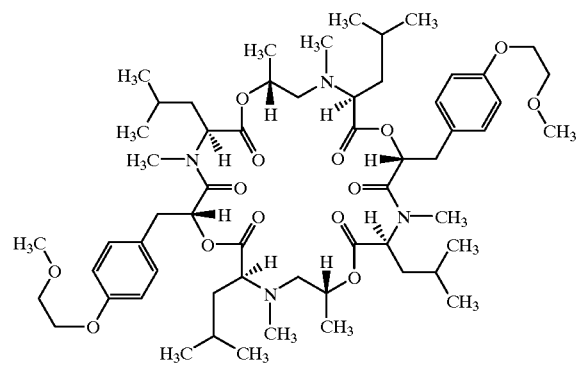

By the method of Example 16, a solution of 84 mg (0.0881 mmol) of 8,20-bis-(4-hydroxybenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 15) in 2 ml of DMF was allowed to react with 146.9 mg (99.4 µl; 1.057 mmol) of 1-bromo-2-methoxyethane in the presence of 73.05 mg (0.529 mmol) of potassium carbonate and 131.5 mg (0.811 mmol) of sodium iodide in 5 ml of DMF at 100° C. for 18 h. The mixture was cooled, concentrated under reduced pressure, taken up in water and extracted with dichloromethane, and the combined extracts were dried and concentrated. This gave 77.6 mg of crude product. 106.6 mg of crude product from two batches was freed of components insoluble in acetonitrile. The resulting 84.4 mg were then purified further by semipreparative HPLC (RP phase; acetonitrile/water). One of the last fractions gave 13.5 mg of 5,11,17,23-tetraisobutyl-2,4,10,14,16,22-hexamethyl-8,20-bis-[4-(2-methoxyethoxy)-benzyl]-1,7,13,19-tetraoxa-4,10,16,22-tetraaza-cyclotetracosan-6,9,12,18,21,24-hexaone.

MS(MALDI): m/z (nominal mass): 1069 (M+H$^+$), 1091 (M+Na$^+$).

Example 19

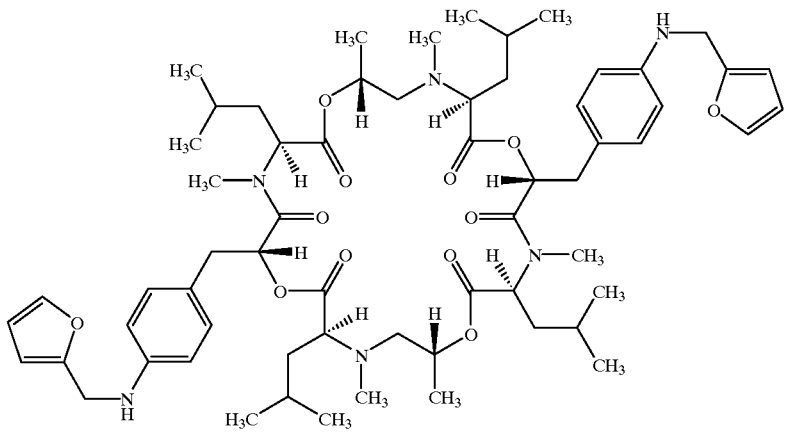

At 0° C., 500 mg (0.526 mmol) of 8,20-bis-(4-aminobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (for example from Example 4) and 59.3 mg (0.957 mmol) of sodium cyanoborohydride were dissolved in 5 ml of methanol, 141.4 mg (1.471 mmol) of furfural were added and the mixture was subsequently stirred at room temperature for 3 h. The same amounts of reagents were then added and the mixture was stirred for another 17 h. The reaction mixture was concentrated and then separated by flash chromatography (column: Ø=4.5 cm, l=15 cm; silica gel; cyclohexane:ethyl acetate=5:1). This gave 407.3 mg (70% of theory) of 8,20-bis-N-[4-(2-furylmethylanino)benzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone.

MS(MALDI): m/z (nominal mass): 1110 (M+H$^+$).

Example 20

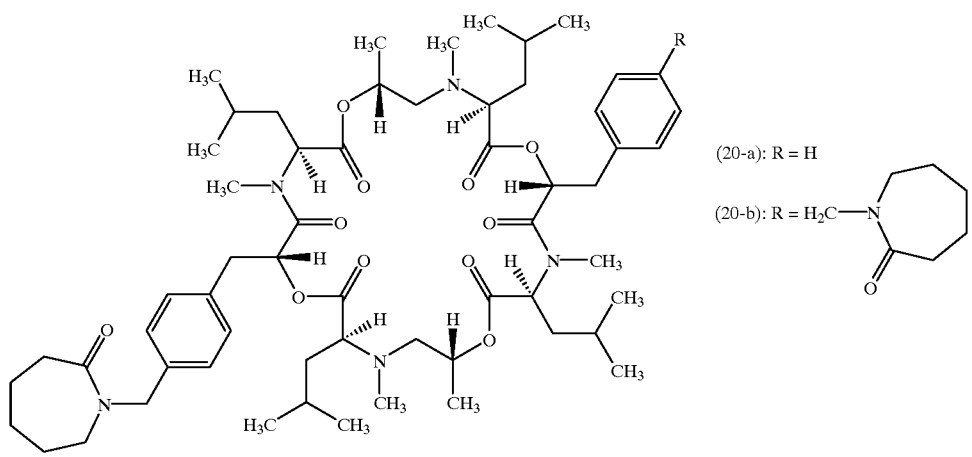

At 0° C., 200 ml of trifluoromethanesulfonic acid were initially charged and 20 g (0.0217 mol) of 8,20-dibenzyl-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (1-b) (for example from Ex. 1) and 6.2 g (0.0434 mmol) of N-hydroxymethyl-ε-caprolactam were added successively, and the mixture was stirred at room temperature for 20 h. The mixture was then poured onto ice, neutralized by addition of solid sodium bicarbonate and subsequently extracted with dichloromethane. The combined extracts were washed with little water, dried and concentrated. The resulting 26 g of crude product were separated by MPLC. The first main fraction gave 1.22 g of singly amidoalkylated compound 20-benzyl-8-[4-(2-oxoazepan-1-ylmethyl)benzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (20-a). After intermediate fractions of a total of 4.21 g, 5.59 g of doubly amidoalkylated compound 8.20-bis-[4-(2-oxoazepan-1-ylmethyl)benzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (20-b) were obtained.

MS (ESI): m/z (nominal masses): Monoalkylated product (16-a): 1045 (M+H$^+$); dialkylated product (16-b): 1170 (M+H$^+$).

Example 21

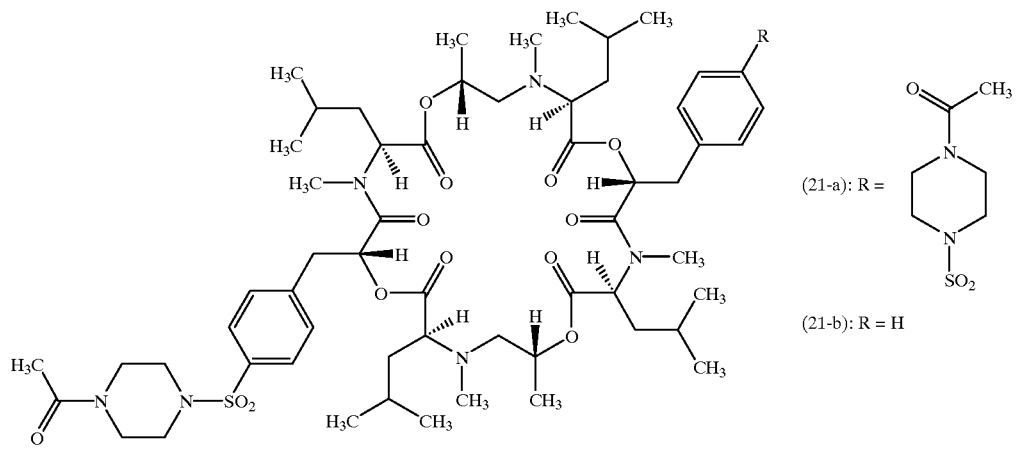

At 0° C., 1.00 g (1.085 mmol) of 8,20-dibenzyl-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (1-b) (for example from Ex. 1) were initially charged in 15 ml of dichloromethane, 8.85 g (5.06 ml; 75.98 mol) of chlorosulfonic acid were added dropwise with cooling and the mixture was stirred at room temperature for 2 h. The mixture was subsequently poured onto ice and extracted with ethyl acetate and dichloromethane. The combined extracts were dried and concentrated. The residue was dissolved in 20 ml of dichloromethane and a solution of 0.370 mg (0.494 ml; 2.87 mmol) of ethyl diisopropylamine, 69.1 mg (0.564 mmol) of 4-dimethylaminopyridine and 612.2 mg (4.77 mmol) of N-acetylpiperazine in 10 ml of dichloromethane was added dropwise at room temperature, and the mixture was subsequently stirred overnight. The reaction mixture was diluted with further dichloromethane, washed with water, dried and concentrated. The residue was separated by flash chromatography (column: Ø=4.5 cm, l=20 cm; silica gel; ethyl acetate:methanol =9:1). This gave 379.3 mg (25% of theory) of 8,20-bis-[4-(4-acetylpiperazin-1-yl)-sulfonylbenzyl]-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (21-a) and subsequently 226.4 mg of 8-[4-(4-acetylpiperazin-1-yl)-sulfonyl-benzyl]-20-(4-sulfobenzyl)-5,11,17,23-tetraisobutyl-2,4,10,14,16,22-hexamethyl-1,7,13,19-tetraoxa-4,10,16,22-tetraaza-cyclotetracosan-6,9,12,18,21,24-hexaone (21-b).

MS (ESI): m/z (nominal masses): Compound (21-a): 1300 (M+H$^+$); Compound (21-b): 1190 (M+H$^+$).

Examples 22 to 39

By the methods of Examples 1 to 21 and/or in accordance with the general ration protocol, the compounds of the formula (I-1-a) listed in Table 1 below obtained.

TABLE 1

(I-1-a)

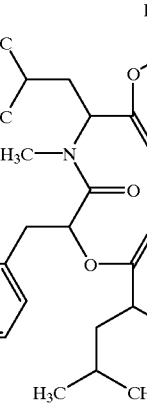

| Ex. No. | X$^2$ | W$^1$ | W$^2$ | MS: m/z; (M + H)$^+$; (M + Na)$^+$ |
|---|---|---|---|---|
| 22 | O | NO$_2$ | NO$_2$ | 1025; 1047 |
| 23 | O | NH$_2$ | NH$_2$ | 965 |
| 24 | O | 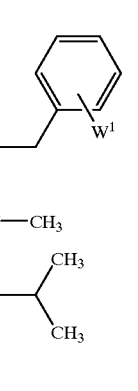 | 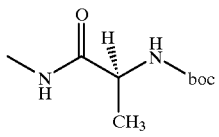 | 1105; 1127 |
| 25 | H$_2$ | 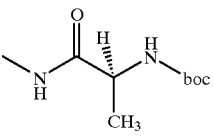 | 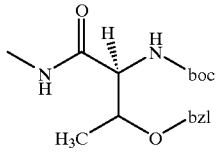 | 1194 (-boc) |
| 26 | H$_2$ | 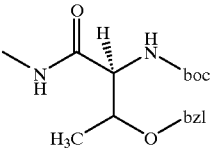 | | 1533 |

TABLE 1-continued (I-1-a)

| Ex. No. | X² | W¹ | W² | MS: m/z; (M + H)⁺; (M + Na)⁺ |
|---------|-----|-----|-----|------------------------------|
| 27 | H₂ | N-methyl prolinamide, N-boc | N-methyl prolinamide, N-boc | 1345 |
| 28 | O | N-methyl alaninamide, N-boc | N-methyl alaninamide, N-boc | 1307 |
| 29 | O | N-methyl tyrosinamide, N-boc | N-methyl tyrosinamide, N-boc | 1671 |
| 30 | O | N-methyl threoninamide O-bzl, N-boc | N-methyl threoninamide O-bzl, N-boc | 1547 |
| 31 | O | N-methyl prolinamide, N-boc | N-methyl prolinamide, N-boc | 1359 |
| 32 | O | N-methyl phthalimide | N-methyl phthalimide | 1225 |
| 33 | H₂ | N,N-dimethyl furfurylamine | N,N-dimethyl furfurylamine | 1139; 1161 |

TABLE 1-continued (I-1-a)

[Structure of cyclic depsipeptide (I-1-a) shown]

| Ex. No. | $X^2$ | $W^1$ | $W^2$ | MS: m/z; $(M + H)^+$; $(M + Na)^+$ |
|---|---|---|---|---|
| 34 | $H_2$ | N-methyl-(thiophen-2-ylmethyl)amino | N-methyl-(thiophen-2-ylmethyl)amino | 1143; 1165; 1181 (+K) |
| 35 | $H_2$ | N,N-dimethyl-(thiophen-2-ylmethyl)amino | N,N-dimethyl-(thiophen-2-ylmethyl)amino | 1171; 1193; 1209 (+K) |
| 36 | $H_2$ | N-ethyl-2-chloroacetamido | N-ethyl-2-chloroacetamido | 1131; 1153 |
| 37 | $H_2$ | 1-ethyl-2-oxopyrrolidinyl | H | 1018; 1040; 1156 |
| 38 | O | 1-ethyl-2-oxoazepanyl | 1-ethyl-2-oxoazepanyl | 1185; 1207 |
| 39 | O | 1-ethyl-2-oxoazepanyl | H | 1060, 1082, 1098 (+K) |

Abbreviations:
boc = tert-butoxycarbonyl
bzl = benzyl

Use Example

Example A

Haemonchus contortus/sheep

Sheep experimentally infected with Haemonchus contortus were treated after expiry of the prepatency time of the parasite.

The active compounds were administered orally in gelatin capsules as pure active ingredient.

The efficacy is determined by quantitatively counting the nematode eggs excreted with the feces before and after treatment.

Complete cessation of oviposition after treatment means that the nematodes have been expelled or are so damaged that they no longer produce eggs (Dosis effectiva).

The following results were obtained:

| Active compound Preparation Example No. | effective dose in mg/kg |
|---|---|
| 1-b | <1 |
| 5, 7-b | <1 |
| 7-c | <1 |
| 7-d | <1 |
| 6 | <1 |
| 1-c, 2 | <1 |
| 14 | <1 |
| 16-a | <1 |
| 16-c | <1 |
| 17-a | <1 |
| 19 | <1 |
| 21-b | 1 |
| 22 | <1 |
| 24 | <1 |
| 37 | <1 |

What is claimed is:

1. Deoxycyclodepsipeptides of the formula (I)

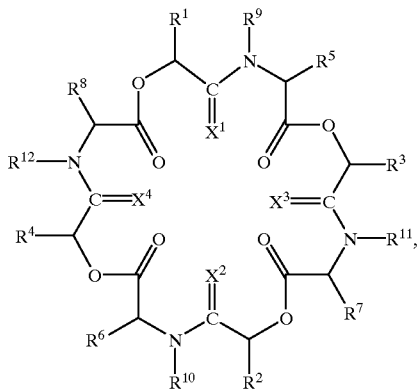

(I)

in which
$C=X^1$, $C=X^2$, $C=X^3$ and $C=X^4$ independently of one another each represent one of the groups CO, CS or $CH_2$, where at least one of these groups represents $CH_2$,
$R^1$ and $R^2$ independently of one another each represent hydrogen, alkyl, hydroxymethyl or alkoxymethyl,
$R^3$ and $R^4$ independently of one another each represent alkyld, phenyl or benzyl, each of which is optionally mono- or polysubstituted by radicals W, where
W represents halogen, nitro, cyano, carbonyl, alkoxycarbonyl, alkyl, —$CH(R^{13})NR^{14}R^{15}$, alkenyl, alkoxycarbonylalkenyl, alkynyl, alkoxycarbonylalkynyl, hydroxyl, alkoxy, alkoxyalkoxy, alkoxyalkoxyalkoxy, dialkylaminoalkoxy, optionally substituted aryl, arylalkyl, aryloxy, arylmethoxy, heterocyclylmethoxy, —$NR^{16}R^{17}$, —$SO_2$—$NR^{16}R^{17}$, —$SR^{18}$, —$S(O)R^{18}$ or —$S(O)_2R^{18}$,
$R^{13}$ represents hydrogen or carboxyl,
$R^{14}$ represents hydrogen, alkyl, optionally halogen-substituted alkylcarbonyl or benzoyl or
$R^{13}$ and $R^{14}$ together represent a radical —$(CH_2)_n$—CO—, where n=2, 3 or 4,
$R^{15}$ represents hydrogen, alkyl, optionally halogen-substituted alkylcarbonyl or benzoyl, or
$R^{14}$ and $R^{15}$ together represent a radical —$(CH_2)_o$—CO—, where o=3, 4 or 5, a diacyl radical of a $C_4$–$C_6$-dicarboxylic acid or optionally halogen-substituted phthaloyl, $R^{16}$ represents hydrogen, optionally halogen-, hydroxyl- or alkoxy-substituted alkyl, heterocyclylmethyl, formyl, alkylcarbonyl or optionally substituted arylmethyl or benzoyl, or the radical —CO—$CR^{19}R^{20}$—$NR^{21}R^{22}$ and
$R^{17}$ represents hydrogen, optionally halogen-, hydroxyl- or alkoxy-substituted alkyl, heterocyclylmethyl, alkylcarbonyl or optionally substituted arylmethyl or benzoyl, or
$R^{16}$ and $R^{17}$ together represent optionally substituted phthaloyl or, together with the linking nitrogen atom, an optionally substituted mono- or polycyclic, optionally bridged and/or spirocyclic, saturated or unsaturated heterocycle which may contain one to 3 further hetero atoms from the group consisting of nitrogen, oxygen and sulfur,
$R^{18}$ represents alkyl or optionally substituted phenyl or benzyl,
$R^{19}$ represents one of the sidechain radicals of a natural or synthetic α-amino acid, where functional groups may optionally be protected,
$R^{20}$ represents hydrogen, alkyl or phenyl, or
$R^{19}$ and $R^{20}$ together represent —$(CH_2)_p$—, where p=2, 3, 4 or 5, or —$(CH_2)_2$—$NR^{23}$—$(CH_2)_2$—, where $R^{23}$ represents alkyl, phenyl or benzyl,
$R^{21}$ represents hydrogen or alkyl, or
$R^{19}$ and $R^{21}$ together represent —$(CH_2)_3$— and —$(CH_2)_4$— and
$R^{22}$ represents hydrogen or a protective group which is acetyl, tertbutoxy carbonyl (Boc), benzyloxycarbonyl (Cbz) or benzyl (Bzl),
$R^5$, $R^6$, $R^7$ and $R^8$ independently of one another each represent hydrogen, optionally amino- or hydroxyl-substituted alkyl, mercaptomethyl, methylthioethyl, carboxymethyl, carboxyethyl, carbamoylmethyl, carbamoylethyl, guanidinopropyl, optionally amino-, nitro-, halogen-, hydroxyl- or methoxy-substituted phenyl or benzyl, naphthylmethyl, indolylmethyl, imidazolylmethyl, triazolylmethyl or pyridylmethyl, where functional groups may optionally be protected, and
$R^9$, $R^{10}$, $R^{11}$ and $R^{12}$ independently of one another each represent hydrogen or optionally substituted $C_1$–$C_4$-alkyl.

2. A process for preparing the deoxycyclodepsipeptides of the formula (I) according to claim 1

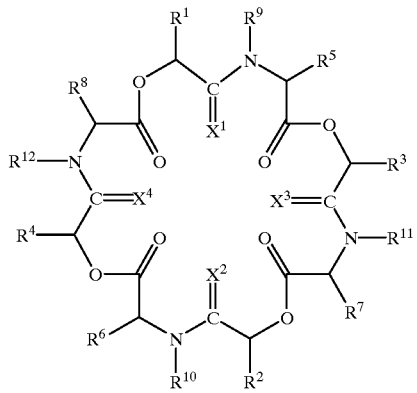

in which
$C=X^1$, $C=X^2$, $C=X^3$ and $C=X^4$ independently of one another each represent one of the groups CO, CS or $CH_2$, where at least one of these groups represents $CH_2$, $R^1$ and $R^2$ independently of one another each represent hydrogen, alkyl, hydroxymethyl or alkoxymethyl, $R^3$ and $R^4$ independently of one another each represent alkyl or phenyl or benzyl, each of which is optionally mono- or polysubstituted by radicals W, where W represents halogen, nitro, cyano, carbonyl, alkoxycarbonyl, alkyl, —CH($R^{13}$)N$R^{14}R^{15}$, alkenyl, alkoxycarbonylalkenyl, alkynyl, alkoxycarbonylalkynyl, hydroxyl, alkoxy, alkoxyalkoxy, alkoxyalkoxyalkoxy, dialkylaminoalkoxy, optionally substituted aryl, arylalkyl, aryloxy, arylmethoxy, heterocyclylmethoxy, —N$R^{16}R^{17}$, —SO$_2$—N$R^{16}R^{17}$, —S$R^{18}$, —S(O)$R^{18}$ or —S(O)$_2R^{18}$, $R^{13}$ represents hydrogen or carboxyl, $R^{14}$ represents hydrogen, alkyl, optionally halogen-substituted alkylcarbonyl or benzoyl or $R^{13}$ and $R^{14}$ together represent a radical —(CH$_2$)$_n$—CO—, where n=2, 3 or 4, $R^{15}$ represents hydrogen, alkyl, optionally halogen-substituted alkylcarbonyl or benzoyl or $R^{14}$ and $R^{15}$ together represent a radical —(CH$_2$)$_o$—CO—, where o=3, 4 or 5, a diacyl radical of a $C_4$–$C_6$-dicarboxylic acid or optionally halogen-substituted phthaloyl, $R^{16}$ represents hydrogen, optionally halogen-, hydroxyl- or alkoxy-substituted alkyl, heterocyclylmethyl, formyl, alkylcarbonyl or optionally substituted arylmethyl or benzoyl or the radical —CO—C$R^{19}R^{20}$—N$R^{21}R^{22}$ and $R^{17}$ represents hydrogen, optionally halogen-, hydroxyl- or alkoxy-substituted alkyl, heterocyclylmethyl, alkylcarbonyl or optionally substituted arylmethyl or benzoyl, or $R^{16}$ and $R^{17}$ together represent optionally substituted phthaloyl or, together with the linking nitrogen atom, represent an optionally substituted mono- or polycyclic, optionally bridged and/or spirocyclic, saturated or unsaturated heterocycle which may contain one to 3 further hetero atoms from the group consisting of nitrogen, oxygen and sulfur, $R^{18}$ represents alkyl or optionally substituted phenyl or benzyl, $R^{19}$ represents one of the sidechain radicals of a natural or synthetic α-amino acid, where functional groups may optionally be protected, $R^{20}$ represents hydrogen, alkyl or phenyl, or $R^{19}$ and $R^{20}$ together represent —(CH$_2$)$_p$—, where p=2, 3, 4 or 5, or represent —(CH$_2$)$_2$—N$R^{23}$—(CH$_2$)$_2$—, where $R^{23}$ represents alkyl, phenyl or benzyl, $R^{21}$ represents hydrogen or alkyl, or $R^{19}$ and $R^{21}$ together represent —(CH$_2$)$_3$— and —(CH$_2$)$_4$— and $R^{22}$ represents hydrogen or a protective group which is acetyl, tertbutoxy carbonyl (Boc), benzyloxycarbonyl (Cbz) or benzyl (Bzl), $R^5$, $R^6$, $R^7$ and $R^8$ independently of one another each represent hydrogen, optionally amino- or hydroxyl-substituted alkyl, mercaptomethyl, methylthioethyl, carboxymethyl, carboxyethyl, carbamoylmethyl, carbamoylethyl, guanidinopropyl, optionally amino-, nitro-, halogen-, hydroxyl- or methoxy-substituted phenyl or benzyl, naphthylmethyl, indolylmethyl, imidazolylmethyl, triazolylmethyl or pyridylmethyl, where functional groups may optionally be protected, and $R^9$, $R^{10}$, $R^{11}$ and $R^{12}$ independently of one another each represent hydrogen or optionally substituted $C_1$–$C_4$-alkyl, characterized in that cyclodepsipeptides which have been prepared by fermentation or synthetically and which have 24 ring members a) are reduced with borane (boron hydride) or complex hydrides in the presence of metal salts, or b) are reacted with a sulfurizing agent and subsequently reduced with complex hydrides in the presence of metal salts and the compounds according to the invention obtained by one of the processes a) or b) are optionally derivatized further.

3. Deoxycyclodepsipeptides of the formula (I)

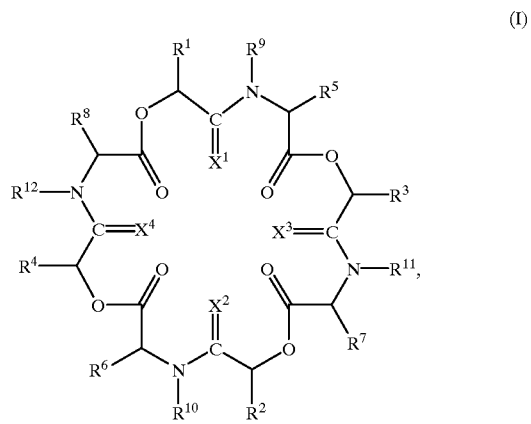

(I)

in which

C=$X^1$, C=$X^2$, C=$X^3$ and C=$X^4$ independently of one another each represent one of the groups CO, CS or CH$_2$, where at least one of these groups represents CH$_2$, $R^1$ and $R^2$ independently of one another each represent hydrogen, $C_1$–$C_6$-alkyl, hydroxymethyl or $C_1$–$C_6$-alkoxymethyl, $R^3$ and $R^4$ independently of one another each represent $C_1$–$C_6$-alkyl or phenyl or benzyl, each of which is optionally mono- or disubstituted by a radical W, $R^5$, $R^6$, $R^7$ and $R^8$ independently of one another each represent hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 4-methoxybenzyl, 2-nitrobenzyl, 3-nitrobenzyl, 4-nitrobenzyl, 2-aminobenzyl, 3-aminobenzyl, 4-aminobenzyl, 3,4-dichlorobenzyl, 4-iodobenzyl, α-naphthylmethyl, β-naphthylmethyl, 3-indolylmethyl, 4-imidazolylmethyl, 1,2,3-triazol-1-yl-methyl, 1,2,4-triazol-1-yl-methyl, 2-pyridylmethyl or 4-pyridylmethyl, where functional groups may optionally be protected, $R^9$, $R^{10}$, $R^{11}$ and $R^{12}$ independently of one another each represent hydrogen, methyl or ethyl, W represents halogen, nitro, cyano, carbonyl, $C_1$–$C_6$-alkoxycarbonyl, $C_1$–$C_6$-alkyl, —CH($R^{13}$)N $R^{14}R^5$, $C_2$–$C_6$-alkenyl, $C_1$–$C_6$-alkoxycarbonyl—$C_2$–$C_4$-alkenyl, $C_2$–$C_6$-alkynyl, $C_1$–$C_6$-alkoxycarbonyl—$C_2$–$C_4$-alkynyl, hydroxyl, $C_1$–$C_6$-alkoxy, $C_1$–$C_6$-alkoxy—$C_1$–$C_6$-alkoxy, $C_1$–$C_6$-alkoxy-$C_1$–$C_6$-alkoxy—$C_1$–$C_6$-alkoxy, di-($C_1$–$C_6$-alkyl)-amino-$C_2$–$C_6$-alkoxy, phenyl, benzyl, phenoxy or benzylmethoxy, each of which is optionally mono- to trisubstituted independently of one another by halogen, nitro, cyano, $C_1$–$C_4$-alkyl, $C_1$–$C_4$-alkoxy, $C_1$–$C_4$-halogenoalkoxy, hydroxyl or amino, heterocyclylmethoxy having a 5- to 6-membered monocycle or 8- to 10-membered bicycle having 1 to four hetero atoms selected from 1 to 4 nitrogen atoms, 1 to 2 oxygen and/or 1 to 2 sulfur atoms, —$NR^{16}R^{17}$, —$SO_2$—$NR^{16}R^{17}$, —$SR^{18}$, —$S(O)R^{18}$ or —$S(O)_2R^{18}$, $R^{13}$ represents hydrogen or carboxyl, $R^{14}$ represents hydrogen, $C_1$–$C_6$-alkyl, optionally fluorine- or chlorine-substituted $C_1$–$C_6$-alkylcarbonyl or benzoyl, or $R^{13}$ and $R^{14}$ together represent a radical —$(CH_2)_n$—CO—, where n=2, 3 or 4, $R^{15}$ represents hydrogen, $C_1$–$C_6$-alkyl, $C_1$–$C_6$-alkylcarbonyl or benzoyl, or $R^{14}$ and $R^{15}$ together represent a radical —$(CH_2)_o$—CO—, where o=3, 4 or 5, a diacyl radical of a $C_4$–$C_6$-dicarboxylic acid or optionally halogen-substituted phthaloyl, $R^{16}$ represents hydrogen, optionally halogen-, hydroxyl- or $C_1$–$C_6$-alkoxy-substituted $C_1$–$C_6$-alkyl, heterocyclylmethyl having a 5- to 6-membered monocycle or 8- to 10-membered bicycle having 1 to four hetero atoms selected from 1 to 4 nitrogen atoms, 1 to 2 oxygen and/or 1 to 2 sulfur atoms, formyl, $C_1$–$C_6$-alkylcarbonyl, benzyl or benzoyl, each of which is optionally mono- to trisubstituted independently of one another by halogen, nitro, cyano, $C_1$–$C_4$-alkyl or $C_1$–$C_4$-alkoxy, or the radical —CO—$R^{19}R^{20}$—$NR^{21}R^{22}$, $R^{17}$ represents hydrogen, optionally halogen-, hydroxyl- or $C_1$–$C_6$-alkoxy-substituted $C_1$–$C_6$-alkyl, heterocyclylmethyl having a 5- to 6-membered monocycle or 8- to 10-membered bicycle having 1 to four hetero atoms selected from 1 to 4 nitrogen atoms, 1 to 2 oxygen and/or 1 to 2 sulfur atoms, represents $C_1$–$C_6$-alkylcarbonyl or represents benzyl or benzoyl, each of which is optionally mono- to trisubstituted independently of one another by halogen, nitro, cyano, $C_1$–$C_4$-alkyl or $C_1$–$C_4$-alkoxy, or $R^{16}$ and $R^{17}$ together represent halogen-, nitro-, cyano-, $C_1$–$C_4$-alkyl- or $C_1$–$C_4$-alkoxy-substituted phthaloyl or, together with the linking nitrogen atom, represent an optionally halogen-, $C_1$–$C_4$-alkyl- or $C_1$–$C_4$-alkoxy-substituted and optionally N-acylated monocyclic heterocycle having 3 to 8 ring members or bicyclic heterocycle having 7 to 11 ring members which is optionally bridged and/or spirocyclic, optionally condensed with one or two carbocyclic ring systems, saturated or unsaturated optionally containing 1 to 3 further hetero atoms from the group consisting of 1 to 3 nitrogen atoms, 1 oxygen atom and 1 sulfur atom, $R^{18}$ represents methyl, ethyl, phenyl or benzyl, each of which is optionally mono- or disubstituted independently of one another by fluorine, chlorine, nitro, methyl, trifluoromethyl or methoxy, $R^{19}$ represents hydrogen, optionally amino- or hydroxyl-substituted $C_1$–$C_4$-alkyl, mercaptomethyl, methylthioethyl, carboxymethyl, carboxyethyl, carbamoylmethyl, carbamoylethyl, guanidinopropyl optionally amino-, nitro-, halogen-, hydroxyl- or methoxy-substituted phenyl or benzyl, or naphthylmethyl, indolylmethyl, imidazolylmethyl, triazolylmethyl or pyridylmethyl, where functional groups may optionally be protected, $R^{20}$ represents hydrogen, $C_1$–$C_4$-alkyl or phenyl, or $R^{19}$ and $R^{20}$ together represent —$(CH_2)_p$—, where p=2, 3, 4 or 5, on —$(CH_2)_2$—$NR^{23}$—$(CH_2)_2$—, where $R^{23}$ represents $C_1$–$C_4$-alkyl, phenyl or benzyl, $R^{21}$ represents hydrogen or $C_1$–$C_4$-alkyl, or $R^{19}$ and $R^{21}$ together represent —$(CH_2)_3$— and —$(CH_2)_4$—, $R^{22}$ represents hydrogen or a protective group which is acetyl, tertbutoxycarbonyl, benzyloxycarbonyl or benzyl.

4. Deoxycyclodepsipeptides of the formula (I)

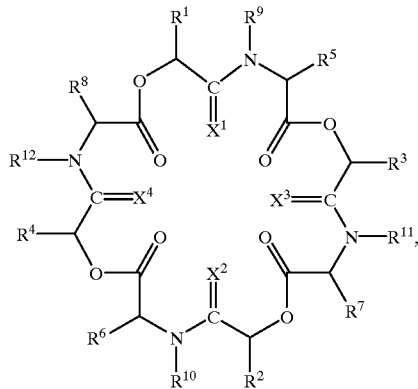

(I)

in which $C=X^1$, $C=X^2$, $C=X^3$ and $C=X^4$ independently of one another each represent one of the groups CO, CS or $CH_2$, where at least one of these groups represents $CH_2$, $R^1$ and $R^2$ independently of one another each represent hydrogen, $C_1$–$C_4$-alkyl, hydroxymethyl or $C_1$–$C_4$-alkoxymethyl, $R^3$ and $R^4$ independently of one another each represent phenyl or benzyl, each of which is optionally each substituted by a radical W, $R^5$, $R^6$, $R^7$ and $R^8$ independently of one another each represent methyl, isopropyl, iso-butyl, sec-butyl, hydroxymethyl, benzyl, or 4-hydroxybenzyl, where hydroxyl groups may optionally be protected, $R^9$, $R^{10}$, $R^{11}$ and $R^{12}$ independently of one another each represent hydrogen or methyl, W represents fluorine, chlorine, bromine, iodine, nitro, cyano, carbonyl, $C_1$–$C_4$-alkoxycarbonyl, $C_1$–$C_4$-alkyl, —$CH(R^{13})NR^{14}R^{15}$, $C_2$–$C_6$-alkenyl, $C_1$–$C_4$-alkoxycarbonyl-$C_2$–$C_4$-alkenyl, $C_2$–$C_4$-alkynyl, $C_1$–$C_4$-alkoxycarbonyl-$C_2$–$C_4$-alkynyl, hydroxyl, $C_1$–$C_4$-alkoxy, $C_1$–$C_4$-alkoxy-$C_1$–$C_4$-alkoxy, $C_1$–$C_4$-alkoxy-$C_1$–$C_4$-alkoxy-$C_1$–$C_4$-alkoxy, di-($C_1$–$C_4$-alkyl)-amino-$C_2$–$C_4$-alkoxy, phenyl, benzyl, phenoxy or benzylmethoxy, each of which is optionally mono- or disubstituted independently of one another by fluorine, bromine, nitro, cyano, $C_1$–$C_4$-alkyl, fluorine- and/or chlorine-substituted methyl or ethyl, $C_1$–$C_4$-alkoxy, trifluoromethoxy, hydroxyl or amino, furylmethoxy, benzofurylmethoxy, thienylmethoxy, pyrrolylmethoxy, indolylmethoxy, imidazolylmethoxy, pyridylmethoxy, —$NR^{16}R^{17}$ or —$SO_2$—$NR^{16}R^{17}$, $R^{13}$ represents hydrogen or carboxyl, $R^{14}$ represents hydrogen, $C_1$–$C_4$-alkyl, benzoyl or $C_1$–$C_4$-alkylcarbonyl which is optionally mono- to trisubstituted by fluorine or chlorine, or $R^{13}$ and $R^{14}$ together represent a radical —$(CH_2)_n$—CO—, where n=2, 3 or 4, $R^{15}$ represents hydrogen, methyl, ethyl, n-propyl, isopropyl, n-butyl, isobutyl or tert-butyl, or $R^{14}$ and $R^{15}$ together represent a radical —$(CH_2)_o$—CO—, where o=3, 4 or 5, a diacyl radical of a $C_4$–$C_6$-dicarboxylic acid or phthaloyl which is optionally mono- or polysubstituted by chlorine or fluorine, $R^{16}$ represents hydrogen, methyl, ethyl, n-propyl, isopropyl, n-butyl, isobutyl, sec-butyl or tert-butyl, methyl, ethyl or n-propyl, each of which is monosubstituted by chlorine, bromine, hydroxyl, methoxy or ethoxy, furylmethyl, benzofuryl methyl, thienylmethyl, pyrrolylmethyl, indolylmethyl, imidazolylmethyl, pyridylmethyl, formyl, $C_1$–$C_4$-alkylcarbonyl or benzyl or benzoyl, each of which is optionally mono- or disubstituted independently of one another by fluorine, chlorine, bromine, iodine, nitro, cyano, $C_1$–$C_4$-alkyl, or $C_1$–$C_4$-alkoxy, or the radical —CO—$CR^{19}R^{20}$—$NR^{21}R^{22}$, $R^{17}$ represents hydrogen, methyl, ethyl, n-propyl, isopropyl, n-butyl, isobutyl, sec-butyl or tert-butyl, methyl, ethyl or n-propyl which are monosubstituted by chlorine, bromine, hydroxyl, methoxy or ethoxy, furylmethyl, benzofurylmethyl, thienylmethyl, pyrrolylmethyl, indolylmethyl, imidazolylmethyl, pyridylmethyl or benzyl which is optionally mono- or disubstituted independently of one another by fluorine, chlorine, bromine, iodine, nitro, cyano, $C_1$–$C_4$-alkyl or $C_1$–$C_4$-alkoxy, or $R^{16}$ and $R^{17}$ together represent phthaloyl which is optionally mono- to tetrasubstituted by fluorine, chlorine or methyl and/or mono- or disubstituted by bromine, nitro, cyano, $C_2$–$C_4$-alkyl, methoxy, or, together with the linking nitrogen atom, an optionally fluorine-, chlorine-, methyl-, ethyl-, n-propyl-, isopropyl-, methoxy- or ethoxy-substituted and optionally $C_1$–$C_4$-alkylcarbonyl-N-acylated monocyclic heterocycle having 3 to 8 ring members or bicyclic heterocycle having 7 to 11 members which is optionally bridged and/or spirocyclic, optionally condensed with one or two carbocyclic ring systems, saturated or unsaturated and may contain 1 to 3 further hetero atoms from the group consisting of 1 to 3 nitrogen atoms, 1 oxygen atom and 1 sulfur atom, $R^{19}$ represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl, 4-hydroxybenzyl, 4-methoxybenzyl, 2-nitrobenzyl, 3-nitrobenzyl, 4-nitrobenzyl, 2-aminobenzyl, 3-aminobenzyl, 4-aminobenzyl, 3,4-dichlorobenzyl, 4-iodobenzyl, α-naphthylmethyl, β-naphthylmethyl, 3-indolylmethyl, 4-imidazolylmethyl, 1,2,3-triazol-1-yl-methyl, 1,2,4-triazol-1-yl-methyl, 2-pyridylmethyl or 4-pyridylmethyl, where functional groups may optionally be protected, $R^{20}$ represents hydrogen, $C_1$–$C_4$-alkyl or phenyl, or $R^{19}$ and $R^{20}$ together represent —$(CH_2)_p$—, where p=2, 3, 4 or 5, or —$(CH_2)_2$—$NR^{23}$—$(CH_2)_2$—, where $R^{23}$ represents $C_1$–$C_4$-alkyl, phenyl or benzyl, $R^{21}$ represents hydrogen or $C_1$–$C_4$-alkyl, or $R^{19}$ and $R^{21}$ together represent —$(CH_2)_3$— and —$(CH_2)_4$—, $R^{22}$ represents hydrogen or a protective group which is acetyl, tert-butoxycarbonyl, benzyloxycarbonyl or benzyl.

5. Deoxycyclodepsipeptides of the formula (I)

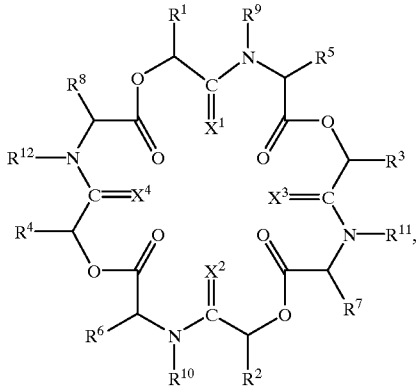

(I)

in which $C=X^1$, $C=X^2$, $C=X^3$ and $C=X^4$ independently of one another each represent one of the groups CO or $CH_2$, where at least one of these groups represents $CH_2$, $R^1$ and $R^2$ independently of one another each represent methyl, hydroxymethyl or methoxymethyl, $R^3$ and $R^4$ independently of one another each represent benzyl which is optionally substituted by a radical W, $R^5$, $R^6$, $R^7$ and $R^8$ independently of one another each represent iso-propyl, iso-butyl or sec-butyl, $R^9$, $R^{10}$, $R^{11}$ and $R^{12}$ each represent methyl, W represents bromine, iodine, nitro, cyano, carbonyl, methoxycarbonyl, ethoxycarbonyl, —$CH(R^{13})$NR$^{14}$R$^{15}$, 2-oxo-pyrrolidin-5-yl, 2-oxo-piperidin-6-yl, 2-methoxycarbonyl-vinyl, 2-methoxycarbonyl-ethynyl, hydroxyl, methoxy, 2-methoxy-ethoxy, 2-dimethylamino-ethoxy, phenyl, benzyl, phenoxy or benzylmethoxy, each of which is optionally mono- or disubstituted independently of one another by fluorine, bromine, nitro, cyano, methyl, ethyl, trifluoromethyl, difluoromethyl, chlorodifluoromethyl, trichloromethyl, methoxy, ethoxy, trifluoromethoxy, hydroxyl or amino, 2-furylmethoxy, 2-thienylmethoxy, 2-pyrrolylmethoxy, —$NR^{16}R^{17}$ or —$SO_2$—NR$^{16}R^{17}$, $R^{13}$ represents hydrogen or carboxyl, $R^{14}$ represents hydrogen, acetyl, chloroacetyl or benzoyl, $R^{15}$ represents hydrogen, or $R^{14}$ and $R^{15}$, together with the linking nitrogen atom represent 2-oxo-pyrrolidin-1-yl, 2-oxo-piperidin-1-yl, 2-oxo-azepan-1-yl, succinimino, maleinimino, dimethylmaleinimino, glutarimino, phthalimino, tetrafluorophthalimino, 4,5-dichlorophthalimino or tetrachlorophthalimino, $R^{16}$ represents hydrogen, methyl, ethyl, n-propyl, isopropyl, 2-chloroethyl, 2-bromoethyl, 2-chloro-1-propyl, 2-hydroxyethyl, 2-methoxyethyl, 2-furylmethyl, 2-thienylmethyl, 2-pyrrolylmethyl, 2-imidazolylmethyl, formyl, acetyl, propionyl, benzyl, 2-chlorobenzyl, 4-chlorobenzyl, benzoyl, 2-chlorobenzoyl, 4-chlorobenzoyl or 4-nitrobenzoyl or the radicals (a) to (I):

(a) 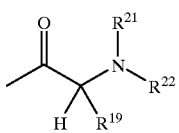

(b) 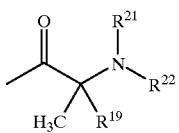

(c) 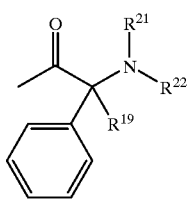

(d) 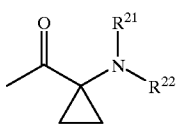

(e) 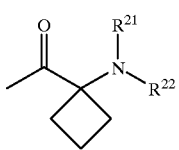

(f) 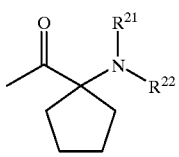

(g) 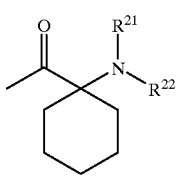

(h) 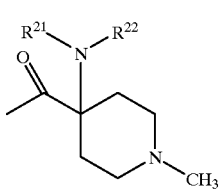

(i) 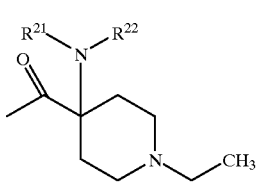

(j) 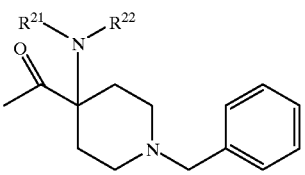

(k) 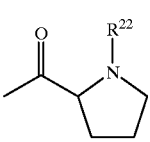

(l) 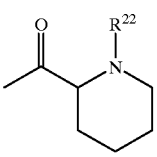

$R^{17}$ represents hydrogen or methyl, ethyl, n-propyl, isopropyl, 2-chloroethyl, 2-bromoethyl, 2-chloro-1-propyl, 2-hydroxyethyl, 2-methoxyethyl, 2-furylmethyl, 2-thienylmethyl, 2-pyrrolylmethyl, 2-imidazolylmethyl, benzyl, 2-chlorobenzyl or 4-chlorobenzyl, or $R^{16}$ and $R^{17}$ together represent phthaloyl, 3-fluorophthaloyl, 3,4-difluorophthaloyl, 4,5-difluorophthaloyl, 3,6-difluorophthaloyl, tetrafluorophthaloyl, 3-chlorophthaloyl, 4,5-dichlorophthaloyl, tetrachlorophthaloyl, 4-nitrophthaloyl, 3-methylphthaloyl, 4-methylphthaloyl, tetramethylphthaloyl, 4-tert-butylphthaloyl or, together with the linking nitrogen atom, an optionally fluorine-, chlorine-, methyl-, ethyl-, n-propyl-, isopropyl-, methoxy- or ethoxy-substituted and optionally n-acetylated monocyclic heterocycle having 5 to 8 ring members or bicyclic heterocycle having 7 to 11 ring members which is optionally bridged, optionally condensed with one or two carbocyclic ring systems, saturated or unsaturated and may contain 1 to 2 further hetero atoms from the group consisting of 1 or 2 nitrogen atoms, 1 oxygen atom and 1 sulfur atom, $R^{19}$ represents hydrogen, methyl, iso-propyl, iso-butyl, sec-butyl, hydroxymethyl, 1-hydroxyethyl, mercaptomethyl, 2-methylthioethyl, 3-aminopropyl, 4-aminobutyl, carboxymethyl, 2-carboxyethyl, carbamoylmethyl, 2-carbamoylethyl, 3-guanidinopropyl, phenyl, benzyl or 4-hydroxybenzyl, $R^{21}$ represents hydrogen or methyl, and $R^{22}$ represents hydrogen or a protective group which is acetyl, tertbutoxycarbonyl, benzyloxycarbonyl or benzyl.

6. Deoxycyclodepsipeptides according to claim 1 of the formulae (I-a) to (I-d)

(I-a) 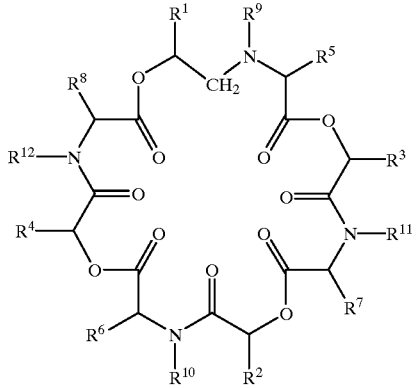

(I-b) 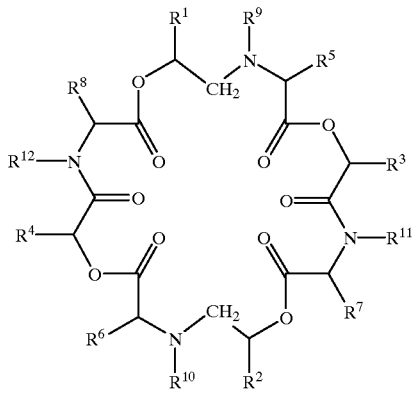

(I-c) 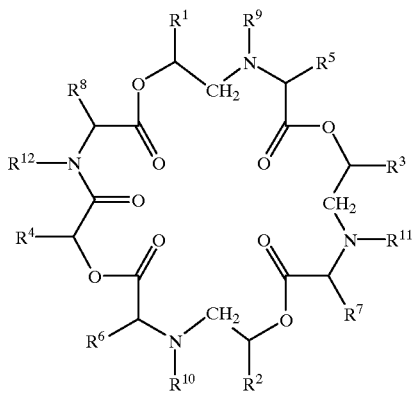

(I-d) 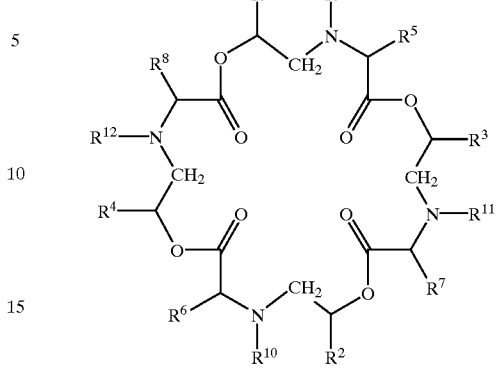

where the radicals $R^1$–$R^{12}$ are as defined in claim 1.

7. Deoxycyclodepsipeptides according to claim 1 of the formula (I-1)

(I-1) 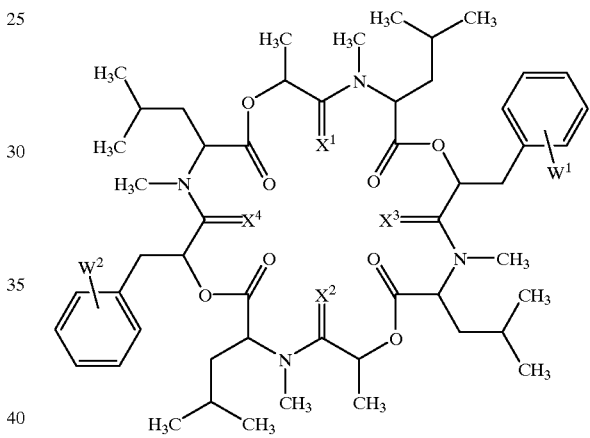

in which
C=$X^1$, C=$X^2$, C=$X^3$ and C=$X^4$ independently of one another are each as defined in claim 1 and
$W^1$ and $W^2$ independently of one another each represent hydrogen or one of the radicals W as set forth in claim 1.

8. Deoxycyclodepsipeptides according to claim 1, in which the optionally substituted and optionally n-acetylated monocylcic heterocycle formed by $R^{16}$ and $R^{17}$ is morpholinyl, pyrrolyl, or piperazinyl.

9. A process for controlling endoparasites comprising contacting them with deoxycyclodepsipeptides of the formula (I) according to claim 1.

10. A method for preparing an endoparasitical composition comprising incorporating therein deoxycyclodepsipeptides of the formula (I) according to claim 1.

11. An endoparasitical composition comprising deoxycyclodepsipeptides of the formula (I) according to claim 1, optionally as a mixture with diluents and additives.

* * * * *